(12) United States Patent
Oldenburg et al.

(10) Patent No.: US 8,962,701 B2
(45) Date of Patent: Feb. 24, 2015

(54) INTEGRATED BIOPROCESSING FOR FUEL PRODUCTION

(75) Inventors: Paul D. Oldenburg, Easton, PA (US); Michel Daage, Hellertown, PA (US); Virginia M. Roberts, Summit, NJ (US); Paul J. Berlowitz, Glen Gardner, NJ (US); David C. Long, Ashburn, VA (US); James R. Bielenberg, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 471 days.

(21) Appl. No.: 13/326,017

(22) Filed: Dec. 14, 2011

(65) Prior Publication Data

US 2013/0158137 A1    Jun. 20, 2013

(51) Int. Cl.
   *C07C 27/00* (2006.01)
   *C07C 51/43* (2006.01)
   *C07C 1/00* (2006.01)

(52) U.S. Cl.
   USPC ............ 518/700; 518/702; 554/175; 585/240

(58) Field of Classification Search
   CPC .... Y02E 50/32; C07C 31/04; C07C 29/1518; C11B 1/10; C11B 1/04; C11C 3/003
   USPC .................... 518/700, 702; 554/175; 585/240
   See application file for complete search history.

(56) References Cited

U.S. PATENT DOCUMENTS

| | | |
|---|---|---|
| 4,044,500 A | 8/1977 | Hitzman |
| 8,030,039 B1 | 10/2011 | Retsina et al. |
| 2007/0249029 A1 | 10/2007 | Marshall et al. |
| 2008/0118964 A1 | 5/2008 | Huntley et al. |
| 2008/0268302 A1 | 10/2008 | McCall |
| 2009/0056201 A1 | 3/2009 | Morgan |
| 2009/0081748 A1 | 3/2009 | Oyler |
| 2009/0181440 A1 | 7/2009 | Rush |
| 2009/0209014 A1 | 8/2009 | Chi et al. |
| 2009/0250401 A1 | 10/2009 | Kotelko et al. |
| 2010/0028962 A1 | 2/2010 | Hu et al. |
| 2010/0081181 A1 | 4/2010 | Berry et al. |
| 2010/0159554 A1 | 6/2010 | O'Rear |
| 2010/0297749 A1 | 11/2010 | Aravanis et al. |
| 2010/0330615 A1 | 12/2010 | Neto |
| 2011/0003357 A1 | 1/2011 | Barclay et al. |
| 2011/0086386 A1 | 4/2011 | Czartoski et al. |
| 2011/0091954 A1 | 4/2011 | Chen et al. |
| 2011/0180455 A1 | 7/2011 | Bouchy et al. |
| 2011/0287497 A1 | 11/2011 | Holtzapple et al. |

FOREIGN PATENT DOCUMENTS

EP    2105495 A1    9/2009

OTHER PUBLICATIONS

International Search Report and Written Opinion from PCT/US2012/24635 dated May 18, 2012.
International Search Report and Written Opinion from PCT/US2012/024637 dated May 23, 2012. (Related Case).

*Primary Examiner* — Jafar Parsa
(74) *Attorney, Agent, or Firm* — Robinson H. W. Clark; David M. Weisberg

(57) ABSTRACT

Systems and methods are provided for enhancing the integration of processes for recovering products from algae-derived biomass. The enhanced process integration allows for increased use of input streams and other reagents that are derived from renewable sources. This increases the overall renewable character of the products extracted from the algae-derived biomass. The process integration can include exchange of input streams or energy between an algae processing system and a system for processing non-algal biomass. One example of improving process integration is using oxygenates that are generated in a renewable manner as a reagent for enhancing the algae processing system.

19 Claims, 5 Drawing Sheets

INTEGRATED BIOPROCESSING FOR FUEL PRODUCTION

FIELD OF THE INVENTION

This invention relates to integrated processing of algae to form fuels, lubricants, chemical products, and/or other products having a renewable character.

BACKGROUND OF THE INVENTION

Conventional production of fuels and lubricants is still dominated by conversion of mineral petroleum feeds into desired products. In order to supplement and/or replace the conventional sources with renewable forms of energy, a variety of problems must be overcome.

One alternative to conventional fuels and lubricants is to produce comparable fuels and lubricants based on biomass. One potential advantage of biomass based fuels and lubricants is that the resulting product may be compatible with existing infrastructure and technologies. Ideally, biomass based fuels and lubricants would be used in a "drop-in" fashion in place of conventional products, allowing the use of a renewable product without having to modify existing equipment. Another potential use would be producing blending stock compatible with conventional fuels and lubricants.

Published U.S. Patent Application 2009/0081748 describes an integrated process and system for production of biofuels using algae. Processes are described for producing a variety of products, including a biodiesel product and an ethanol product.

SUMMARY OF THE INVENTION

In the present invention, systems and methods are provided for enhancing the integration of processes for recovering products from algae-derived biomass. The enhanced process integration allows for increased use of input streams and other reagents that are derived from renewable sources. This, in turn, increases the overall renewable character of the products extracted from the algae-derived biomass. The process integration can include exchange of input streams or energy between an algal biomass processing system and a system for processing non-algal biomass.

First, a method for generating a fuel or fuel blending product from algal derived biomass that is integrated is provided that integrates a gasification process. The method includes providing a feed comprising algae-derived biomass from an algae growth environment. A fuel or fuel blending product and a residual product are recovered from the algae-derived biomass. Optionally, an oxygenate generated by another process in a biomass processing system can be used as a reagent for recovery of the fuel or fuel blending product. A gasification process is performed on at least a portion of the residual product. The gasification process results in at least a gas phase output stream and a gasification residue stream. The gas phase output stream comprises $H_2$ and CO. The gas phase output stream is then purified by removing at least a portion of one or more contaminant compounds different from $H_2$ and CO. For example, $NH_3$ can be removed from the gas phase output stream, or both $NH_3$ and $CO_2$ can be removed to form a second gas phase output stream. Optionally, the removed contaminant compounds can be recycled for use as a nutrient for algae and/or other biomass growth. At least a portion of the purified gas phase output stream is converted into one or more organic molecules. The conversion can correspond to a methanol synthesis reaction, direct fermentation to form ethanol, a Fischer-Tropsch synthesis reaction, or another reaction that benefits from an input stream containing $H_2$ and CO.

Second, alternatively or in addition, another method for generating a biofuel is provided. The method includes growing algae in an algae growth environment. A first fuel or fuel blending product and a residual product are recovered from an algae-derived biomass feed from the algae growth environment. A second fuel or fuel blending product and a second residual product are recovered from a second biomass feed. A gasification process is performed on at least a portion of the second residual product. The gasification process produces at least a first gas phase output stream and a gasification residue, the first gas phase output stream comprising $NH_3$, $CO_2$, or a combination thereof. At least a portion of the first gas phase output stream or the gasification residue is recycled to the algae growth environment.

Any of the methods described above can be performed by a biofuels production system. Further, any of the methods described above can be performed alone or in combination. Accordingly, another aspect of the invention is a biofuels production system that performs one or both of the methods described above.

DETAILED DESCRIPTION OF THE PREFERRED EMBODIMENTS

Overview

Figure 1:
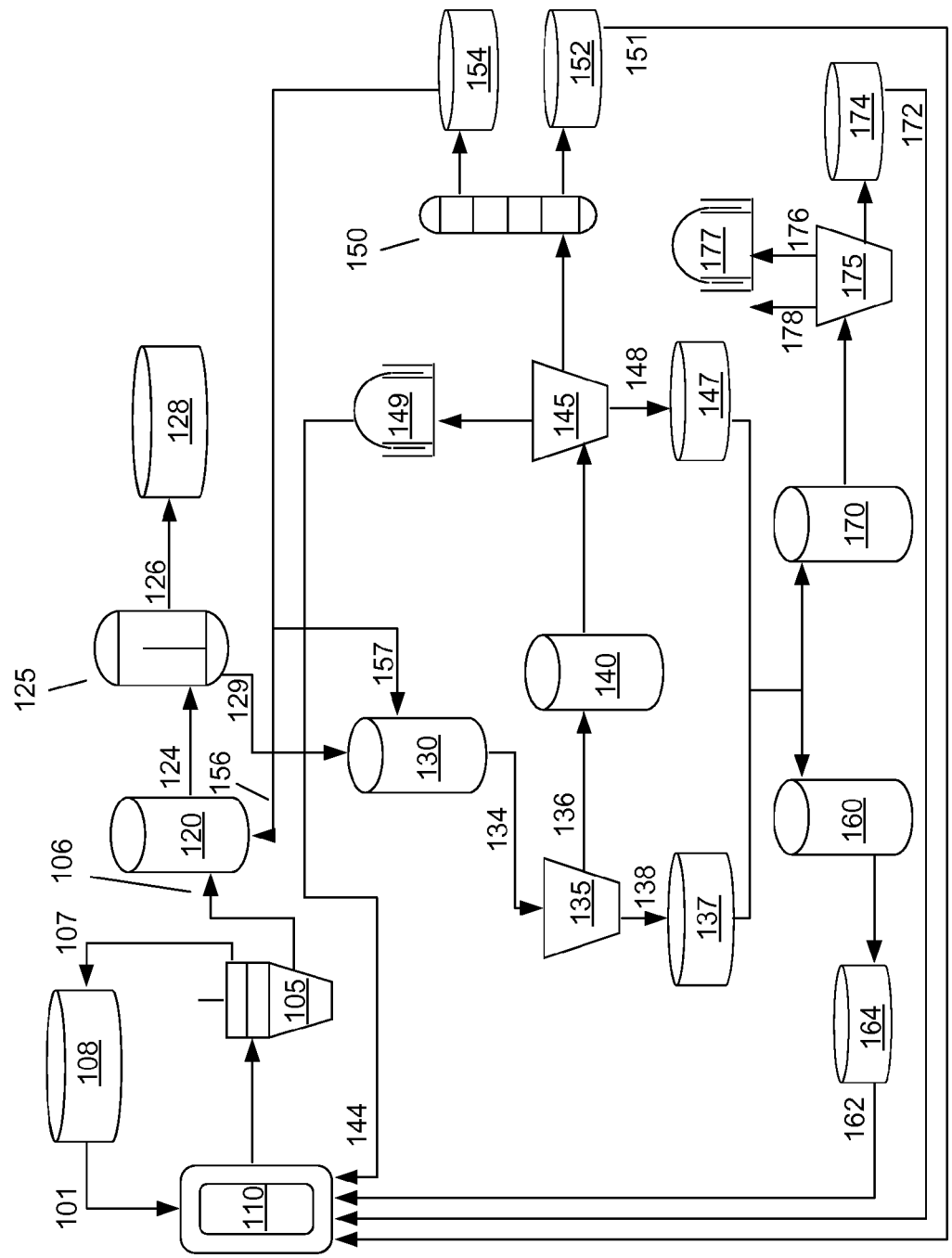
FIG. 1 depicts a reaction system suitable for performing a process according to one aspect of the invention.

Generation of fuels from biological sources is an area of increasing interest for supplementing and/or replacing conventional fossil fuels. Currently, most fuels generated from biological sources are oxygenated fuels such as ethanol, which are intended to supplement the fuel pool for gasoline powered engines. An increasing amount of diesel based on biological sources is also being generated. Fuels, lubricants, and other products from biological sources are based in part on carbon and energy (sunlight) captured from the environment. Such fuels, lubricants, and other products are sometimes referred to as "renewable" products.

Unfortunately, conventional methods for generating renewable products from biological sources still suffer from a variety of drawbacks. One difficulty is that conventional renewable products are typically less than completely renewable in character. The production of ethanol from corn provides an example. Corn-based ethanol is often considered a renewable fuel, as the corn incorporates carbon from the surrounding environment. Thus, the carbon dioxide emitted from burning corn-based ethanol represents carbon originally extracted from the environment. The energy content of the corn is also based on sunlight. Generating ethanol from corn, however, requires a variety of process steps. First, corn seed must be planted. This typically involves operating large farm equipment powered by an engine running on a conventional, non-renewable diesel or gasoline fuel. Such farm equipment running on non-renewable fuel is also used during growth and harvesting of the corn. The harvested corn is then processed in a distillery or other plant capable of extracting sugars/starches from the corn and fermenting the extracted sugars/starches to make ethanol. The fermentation is performed at elevated temperature, and typically is powered by burning a non-renewable fossil fuel. Distillation to concentrate the ethanol is also typically powered by burning fossil fuels. Additionally, the extraction process may involve operating mechanical equipment that is powered by a non-renewable fuel source.

Based on the above example, determining the renewable character of a product should involve more than simply considering the carbon and energy source of the product itself. $CO_2$ generated by burning corn-based ethanol corresponds to carbon atoms that were extracted from the environment during growth of the corn. However, making corn-based ethanol involves a variety of other sources of $CO_2$ emissions. In addition to powering farm and processing equipment, the fermentation process also typically involves burning substantial amounts of fuel. All of this additional fuel burning generates $CO_2$ from non-renewable sources. As a result, even though $CO_2$ generated by burning corn-based ethanol has a renewable character, a substantial amount of non-renewable $CO_2$ is generated prior to combustion of the ethanol. If this additional non-renewable $CO_2$ is accounted for, the apparent renewable character of the corn-based ethanol is reduced. Similarly, it is clear that conventional ethanol generation from corn involves a substantial input from non-renewable energy sources. This reduces the renewable character of the energy derived from corn-based ethanol.

A variety of obstacles remain on the path to generating renewable products from biologic sources. Each problem that is addressed provides another step along that path. Solutions are provided for one or more problems related to increasing the renewable character of a fuel, lubricant, or other product derived from an algae (or other biomass) source. The solutions are based on various methods for algae growth and processing for product extraction with increased process integration. The increased process integration may include increasing the number of renewable inputs used during algae processing, improving the use of by-products generated during algae processing, incorporating feeds and/or processes into the algae processing based on additional forms of biomass, or a combination thereof. For example, integration among biofuel producing processes as described herein can provide synergisms that improve overall energy efficiency, that reduce $CO_2$ emitted to the atmosphere from non-biological (i.e., non-renewable) sources, that improve the ratio of energy output to energy input, and/or that reduce overall greenhouse gas production.

In certain aspects of the invention, enhanced process integration is provided by processing the algae or algae products using reagents derived from a biological source. During algae growth, the algae will produce one or more organic products that represent a desired product for harvesting and separation. Typically, the desired organic product(s) will be based on distillate boiling range molecules, although lighter or heavier molecules may also be produced by some forms of algae. The desired organic product molecules may be suitable for use directly, or the desired product molecules can undergo further processing to make a fuel, lubricant, or other product. Any further processing of a desired product molecule may result in a product with a lower boiling point or higher boiling point. For example, the desired products from some types of algae are fatty acids (FA) or triacyl glycerides (TAG). Fatty acids can be converted to higher boiling fatty acid alkyl esters by combining the fatty acids with molecules that contain one or more alcohol groups. Similarly, distillate boiling range molecules from an algae source could be isomerized or cracked to form a lower boiling range product.

After extracting the desired product from an algae sample, a portion of residual biomass will be left behind. This residual biomass will often include fermentable material or potentially fermentable material. The residual biomass may also contain material that can be processed in aerobic or anaerobic digestion to form other products such as methane or hydrogen. The amount of fermentable material can vary depending on the conditions for extraction of the desired product. In some cases, the amount or weight percent of (potentially) fermentable material in the residual biomass may be too low for a fermentation process to be economically viable.

When sufficient fermentable material is present in the residual biomass, fermenting at least a portion of the residual biomass can generate one or more types of oxygenates. Alternatively, other types of biomass may be used for generating oxygenates. These oxygenates, such as alcohols or organic acids, can be used to assist with a various parts of the algae processing. Examples of uses for the oxygenates include use as reagents for extracting products from the algae, use as reagents for converting potentially fermentable residual product materials into fermentable material, or use as reagents in converting distillate boiling range molecules into another form. Creating additional reagents from renewable materials increases the overall renewable character of the final products.

In another aspect of the invention, solutions are provided for reducing the amount of non-biologic $CO_2$ incorporated into a product. To achieve desirable growth rates, conventional algae growth systems typically include a $CO_2$ source in addition to and/or in place of atmospheric $CO_2$. Unfortunately, this additional $CO_2$ source is often derived from burning of fossil fuels, such as an exhaust $CO_2$ stream from a power plant or a refinery. Methods are provided for reducing or eliminating the amount of non-renewable $CO_2$ required for algae growth while still maintaining desirable algae growth rates.

Reducing the amount of non-biologic $CO_2$ may also reduce the overall amount of greenhouse gases generated during algae growth and processing. Fermentation processes for making oxygenates during algae processing represent a source of $CO_2$. If the $CO_2$ from fermentation is allowed to escape, it represents lost $CO_2$ that re-enters the environment without contributing value as a fuel. Capturing and recycling this $CO_2$ provides a way to reduce the amount of non-renewable $CO_2$ needed for algae growth. On a larger scale, $CO_2$ from other biomass processing can be used. For example, an algae processing system can be located near a processing system for another type of biomass, such as an ethanol plant. The $CO_2$ generated from fermentation (or another process) from a co-located plant can provide some or all of the $CO_2$ need for algae growth. This increases the renewable character of the products derived from the algae growth and processing. This also reduces the $CO_2$ emissions from the co-located process.

As an example, the conversion of sugar (from any source) to ethanol by yeast takes one molecule of stoichiometry $C_6H_{12}O_6$ and converts it to two $C_2H_5OH$ molecules (ethanol) and two $CO_2$ molecules. The two $CO_2$ molecules are typically lost to the environment. As a result, one third of the total carbon fixated by the original biological source of the sugar (such as corn starch or algae biomass) is lost to the environment. Instead of losing this carbon to the environment, the invention allow this carbon to be recycled for use in algae growth for eventual conversion into fuels or other products.

This increases the overall carbon efficiency of the algae growth process while reducing the production of greenhouse gases.

Exchanging $CO_2$ is one example of how multiple processes for generating renewable products can be integrated. Other types of process integration can be used as well. Some process integration options involve introducing additional non-algae biomass into an algae processing system. Other process integration options can allow for exchange of heat, feedstock, or reagents between processes.

Still another potential advantage of process integration is the reduction of fertilizer use in algae growth. In addition to carbon, algae also require nitrogen, phosphorous, and various trace minerals as nutrients for growth. Many desired products from algae growth and processing are hydrocarbons that do not include nitrogen, phosphorous or trace metals. Since the nitrogen, phosphorous, and trace minerals are not incorporated into products, these potential nutrients can be available for reuse in growing more algae.

Yet another potential advantage from process integration is improved energy use by integrating heat and/or mechanical energy between processes. A number of biofuel processes require heat to perform preprocessing. An example is enzyme hydrolysis of starches and cellulose that is often performed at 50° C. to 80° C. In a non-integrated facility, the heat for maintaining the processing temperature is typically provided by burning fossil fuels. The heat required for this process can instead by provided by using low level waste heat from hydrothermal processing of algae. Similar types of heat exchange can also be used for distillations that are performed at temperatures below 100° C. In addition to improved heat exchange, any combustion that is performed for heat generation can be powered by waste gases generated during anaerobic digestion of residual algal biomass. Such anaerobic digestion also provides $CO_2$ for recycle to an algae growth stage. Optionally, heat exchange can also be used between systems for processing two different types of biomass.

In another aspect of the invention, additional process integration can be achieved by using gasification to process residual biomass and/or other types of biomass. Gasification typically involves exposing a feed to elevated temperatures in an environment with less $O_2$ than is required for complete combustion of the feed. This generates a variety of products, including $NH_3$, $CO_2$, CO, and $H_2$. A solid gasification residue typically is also created. The $NH_3$ and $CO_2$ can be separated out as nutrients for algae growth and/or growth of other types of biomass. The CO and $H_2$ are useful as a feed to various processes, such as methanol production or Fischer-Tropsch synthesis. Alternatively, the CO and $H_2$ can be fermented directly to ethanol or other small oxygenates by various microorganisms. Methanol is useful as a reagent for synthesis of fatty acid methyl esters (FAME) and can also be used in production other chemicals or gasoline. In addition to providing alkanes, a Fischer-Tropsch synthesis process generates an aqueous by-product that includes a mixture of oxygenates, such as alcohols and organic acids that contain from one to three carbon atoms. The oxygenates in the by-product can be used as a reagent during hydrothermal processing of algae or other biomass. The gasification residue can undergo further processing, such as an acid wash, to allow for recovery phosphorous, trace metals, and any other nutrients present in the gasification residue. Although high temperatures are required to perform gasification on biomass, gasification can improve the ability to recycle most or all of the material present in a biomass input. This allows for reduced generation of greenhouse gases as well as reducing the amount of nutrients required for algae growth and/or growth of other biomass. In addition, $CO_2$ rich gas streams can be used as a feed for an algae pond. The $CO_2$ gas streams can correspond to $CO_2$ generated either initially or during various stages of gasification and subsequent processes. Residual gas streams (such as $H_2$ and/or CO) can be burned for heat and/or power and used in other parts of the combined processes.

Definitions

The "distillate boiling range" is defined herein to include molecules that boil from about 212° F. (100° C.) to about 1100° F. (593° C.), preferably about 250° F. (121° C.) to 750° F. (399° C.), and more preferably from about 300° F. (149° C.) to about 700° F. (371° C.). Narrower ranges within this definition may also be useful in order to meet product specifications such as a diesel product specification or a jet fuel product specification. Note that algae may also produce products outside of the distillate boiling range before, during, or after production of the desired distillate boiling range molecules. Such products outside of the distillate range may include naphtha (gasoline) boiling range molecules, or molecules with boiling points above the distillate boiling range. More generally, a desired product potentially includes any convenient organic species generated by algae. Suitable types of organic molecules include molecules with no functional groups (such as alkanes) as well as molecules with one or more types of functional groups, such as alcohols, amines, organic acids, other heteroatom functional groups, alkenes, aromatics, or other unsaturated functional groups. The desired products generated by algae may be used without further processing. Alternatively, further processing can be used to convert the desired algae products to other molecules, possibly including molecules having a different boiling range or molecules having a similar boiling range but with improved properties. Converted products may also be suitable for use or blending into gasoline for lighter components, or for use or blending into lubricants for molecules heavier than the preferred distillate boiling range.

A "fuel product" is defined herein as a product suitable for use as a fuel either directly or after optional further processing.

A "fuel blending product" is defined herein as a product suitable for blending into a fuel either directly or after optional further processing.

References to a fuel or fuel blending product correspond to a product that satisfies the definition for at least one of a fuel product or a fuel blending product. Note that a fuel product or fuel blending product does not have to be used as a fuel product or fuel blending product to satisfy this definition. Instead, this definition identifies products that are suitable as a fuel product or fuel blending product. For example, ethanol is suitable for use as a fuel product or a fuel blending product, such as by use as a fuel blending product for gasoline. Ethanol is also suitable for other purposes, such as facilitating extraction of products from algae during hydrothermal processing or solvent extraction. In some cases, ethanol generated from processes according to the invention will be used for product extraction or in another use other than use as a fuel. According to the definition herein, such ethanol is considered a fuel or fuel blending product even though it is used for a different purpose.

"Hydrothermal processing" generally refers to treatment of algae in the presence of water under elevated temperature and pressure conditions. Hydrothermal processing can optionally be performed in the presence of hydrogen, a catalyst, and/or additional reagents such as one or more alcohols or acids. Suitable hydrothermal processing conditions are described in greater detail below. Other potential extraction methods, that are not "hydrothermal processing," include solvent extraction, absorption, adsorption, cavitation, cell lysing, and settling.

"Nutrients" are sources of carbon, phosphorous, nitrogen, and trace metals suitable for use in supporting algae growth. Note that a reference to a reagent stream as containing nutrients may indicate that only one of carbon, phosphorous, nitrogen, or trace metals is present. The trace metals can vary depending on the type of algae being grown and/or the type of biomass used to generate the nutrients. If a biomass-derived source of nutrients is not available, various types of fertilizers are available to supply nutrients to an algae growth pond.

"Algal derived biomass or "algae-derived biomass" is defined as biomass that contains algae and/or that contains compounds generated by performing one or more processing steps on algae biomass.

"Non-algal biomass" or "non-algae biomass" is defined as biomass that does not contain algae and/or compounds generated by performing one or more processing steps on biomass that does not contain algae. References herein to sources of non-algal biomass can include any convenient biomass source. Suitable sources include plant biomass sources (including cellulosic and lignocellulosic sources) and animal biomass sources. Other non-algae sources of biomass include waste product sources, such as municipal solid waste (MSW). For example, municipal solid waste can be processed via fermentation to form syngas. The syngas can then be used, for example, to produce ethanol for use in processing of algae.

"Oxygenates" are any organic molecule having four carbons or less that includes at least one functional group containing on oxygen atom, such as alcohols, organic acids, aldehydes, ketones, etc. Specific examples of oxygenates include ethanol, methanol, butanol, isobutanol, ethyl acetate, acetone, and acetic acid.

"Fermentation" generally refers to using a bacterium or yeast to convert an organic starting material into an alcohol or organic acid. This includes both fermentations for producing single oxygenate species as well as multi-stage or multi-product fermentation pathways such as the acetone-butanol-ethanol (ABE) pathway. Typical starting materials include saccharides or other sugars. The saccharides or sugars consumed by the bacteria or yeast may be derived from larger molecules, such as starch, cellulose, or other polysaccharides. Prior to consumption by the bacteria or yeast, the larger molecules are converted into fermentable saccharides or sugars by hydrolysis or another mechanical, chemical, or enzymatic pre-treatment process.

The term "fermentable material" is broadly defined herein to include materials such as polysaccharides which can be converted to fermentable material by hydrolysis or another suitable pre-treatment process.

"Digestion" refers herein to processes for exposing a feed containing organic material to bacteria in an anaerobic environment. The bacteria convert the feed material to a digestion product that is suitable for further use. Typical digestion products include hydrogen, small volatile organic molecules such as methane, $CO_2$, and a variety of compounds containing phosphorous, nitrogen, and/or trace metals. The hydrogen and small organic molecules are typically suitable for use as a fuel while the $CO_2$ and other residual compounds can be recycled to an algae growth pond as nutrients.

As noted above, one potential source of nutrients is to generate nutrients from a biomass source. After processing to extract desired products, and optionally after fermentation to make oxygenates, a portion of residual biomass will remain. A portion of this residual biomass will typically correspond to phosphorous compounds, nitrogen compounds, and other trace metals in some form. This residual biomass can be converted into a form suitable for use as nutrients by an anaerobic digestion process.

Gasification is another option for converting residual biomass. Gasification generates a variety of gas phase products such as $CO_2$ and $NH_3$. $CO_2$ rich streams that are generated at various stages during gasification are suitable for introduction into algae ponds to facilitate algae growth. Gasification has the advantage of being tolerant to a wide variety of feedstocks. Suitable gasification feeds can include but are not limited to crop residue, algae residue, municipal solid waste, and virgin lignocellulosic sources. Gasification also typically generates a residual gasification solid that contains other biomass remnants such as phosphorous and trace metals. An additional potential benefit of gasification is use of gasification as a heat or energy source. Although gasification requires elevated temperatures to enable the gasification reactions, the gasification process is generally exothermic. The energy released during gasification can be used as heat for other processes, or the heat can be captured and converted to electricity or another type of energy. This energy can be captured for maintaining optimal algae growth temperatures in ponds where the average temperature is below the optimal growth temperature. Additionally or alternately, this energy can be used to provide heat to hydrothermal processes or other processes. Such heat integration improves efficiency for algae processing and thus improves overall biofuel output.

Optionally, a digestion or gasification process can further include a post-treatment for the phosphorous, nitrogen, and/or trace metal compounds. For example, a post-treatment acid wash may improve the nutrient value of such compounds for use in future algae growth. Such processes will take inorganic nutrients in sold form and make the nutrients water-soluble and bioavailable. The water-soluble and bioavailable nutrients are then suitable for reintroduction to algae growth ponds or potentially as a fertilizer for growing other crops.

Integrated Use of Oxygenates in Product Extraction

One method for enhancing the integration of processes for extraction/production of products from algae is to generate oxygenates for use in processing algae (or other biomass) as part of the overall algae processing system. For example, if hydrothermal processing is used for extraction of desired product molecules from algae, addition of alcohols and/or organic acids can enhance the extraction process. Such alcohols or organic acids can also be used as solvents at various points in an algae processing system. Alcohol extraction provides another alternative for extraction of product molecules, such as distillate boiling range molecules, from algae. Still another option is to use alcohols, ketones, aldehydes, or organic acids as part of the process for breaking down residual biomass after extraction of desired product materials. While breaking down of residual biomass does not directly lead to increased fuel production (and/or production of other products), the hydrolysis of residual biomass does facilitate eventual recycling of $CO_2$ and/or nutrients to algae growth. This reduces waste and increases the overall renewable character of the products generated from algae processing.

FIG. 1 shows a system that includes various options for performing integrated recovery of desired products from an algae source. A system such as shown in FIG. 1 allows the residual biomass from product extraction to be used for generation of oxygenates, such as ethanol or acetic acid. The generated alcohols or acids are optionally used as a reagent for the product extraction process. Alternatively, the generated oxygenates are recycled to a hydrolysis process used to break down the residual biomass prior to fermentation. In either option, the remaining insoluble products and $CO_2$ from the fermentation process are recycled for use in growth of additional algae. The following provides an overview of the system shown in FIG. 1. A more detailed description of individual processes, including variations, is provided later in this document.

In FIG. 1, one or more algae growth ponds 110 allow for growth of algae and formation of desired products. Growth pond 110 receives a variety of inputs. FIG. 1 shows inputs that are generated by other portions of the system for processing the algae. These inputs include water stream 101 and water stream 151, nutrient stream 162 and nutrient stream 172, and $CO_2$ stream 144. All of these streams are optional, depending on the configuration of the algae growth and product recovery system. If desired, the algae growth pond can be optionally supplied with additional water, nutrients, and/or $CO_2$ from external sources. Examples of external sources include crop residues (such as residues from crops not directly involved in biofuel production) or residual biomass not used in animal feed production.

When it is desired to process the algae in a pond for product extraction, the algae is initially dewatered, such as by using a centrifuge 105. Centrifuge 105 generates algae and product stream 106 (with reduced water content) and a side water stream 107. Side water stream 107 can be stored in a water storage tank 108 until growth pond 110 is ready to receive additional water as water stream 101. Alternatively, side water stream 107 can be returned directly to a growth pond, such as growth pond 110. It is noted that algae and product stream 106 may only contain a portion of the algae and product entering centrifuge 105, as some algae and product may be returned to the growth pond 110 with side water stream 107. Other examples of methods for reducing the water content of the algae from a growth pond include, but are not limited to use of, sunlight, rotary dryers, flash dryers, vacuum dryers, ovens, freeze dryers, hot air dryers, microwave dryers and superheated steam dryers.

The algae and product stream 106 with reduced water content is then exposed to processing conditions for extracting a desired product in an oil recovery process 120. Examples of suitable oil recovery processes 120 include hydrothermal processing and alcohol extraction. Extraction is also possible with products (such as fuel or fuel blending products) produced from the algae found in storage vessel 128, optionally after further processing of the products of vessel 128. In some cases, alcohol and/or organic acids for use in oil recovery process 120 are provided as an input stream 156 that is generated by a later process within the system. After oil recovery process 120, the effluent 124 is passed to a separator 125. A portion of effluent 124 is separated out to form a stream 126. Stream 126 includes at least a portion (and preferably at least a majority) of one or more desired products. Preferably, the one or more desired products include molecules suitable for use as fuel or fuel blending products. At least one of the one or more desired products may be a distillate boiling range product. In FIG. 1, stream 126 is passed into a storage tank 128 to await further processing, such as further refinement, purification, or other modification of the product(s). Alternatively, stream 126 can be passed directly to a subsequent process. The remaining portion of effluent 124 exits separator 125 as a residual stream 129. This residual stream may include a variety of materials, including algal husks and other excess solids that remain after recovery of the desired product. Residual stream 129 may also include a portion of the distillate boiling range product due to practical limitations in performing the separation. In the system shown in FIG. 1, the conditions of oil recovery process 120 are selected so that residual stream 129 contains a sufficient amount of starches, saccharides, polysaccharides and other (potentially) fermentable compounds that a subsequent fermentation process is desirable and/or economically viable. Note that residual stream 129 may correspond to only a portion of the residual products from oil recovery process 120. Other residual products may exit oil recovery process 120 in other streams that are not shown.

In FIG. 1, separator 125 (as well as separators 135, 145, and 175) are shown as single separators. This is for convenience in explaining the invention as described in FIG. 1. However, any of the separators described herein can represent one or more separators. For example, some input flows to separators may have more than 2 distinct phases, such as a gas phase, an aqueous phase, an organic or other non-polar phase, and/or a solid phase, or multiples of any of the above phases. Performing a desired separation may require a series of separators to produce desired output flows from an input stream. It is understood that references to using a separator also include using a plurality of separators. Potential separators that can be used as part of a plurality of separators include gas-liquid separators, liquid-solid separators (such as settling tanks or centrifuges), and separators for separating immiscible or partially miscible liquid phases.

Residual stream 129 can be converted into one or more streams useful as inputs at other locations in the system. To begin this conversion, residual stream 129 is passed into a hydrolysis process 130 or another type of fermentation pretreatment process. A pretreatment is then performed on the residual stream to release fermentable material. Hydrolysis process 130 can represent a chemical hydrolysis process, an enzymatic hydrolysis process, or a combination thereof. Preferably, hydrolysis process 130 can include the use of an alcohol or organic acid 157 that is provided by another process in the system. Hydrolysis process 130 (or other fermentation pretreatment process) generates a water-soluble product of hydrolyzed polysaccharides and other hydrolyzed soluble compounds that are suitable for fermentation. Hydrolysis process 130 also generates an insoluble by-product. The outputs shown for hydrolysis process 130 are only representative, and additional water-soluble product and/or insoluble by-product streams may also be generated.

The hydrolyzed product 134 from hydrolysis process 130 is then passed into a separator 135. Of course, if another type of pretreatment is used, the product from the alternative type of fermentation pretreatment process is passed into the separator. Separator 135 separates the hydrolyzed product into a water soluble product 136 and an insoluble by-product 138. The insoluble by-product can optionally be stored 137 prior to further processing. It is noted that the aqueous hydrolyzed product 136 may also include non-fermentable material. Similarly, a portion of fermentable material may be retained in insoluble by-product 138.

At least a portion of water-soluble product 136 is then passed into a fermenter 140 to convert hydrolyzed soluble compounds (such as saccharides) into oxygenates, such as alcohols, aldehydes, ketones, or organic acids. The fermentation is performed in any convenient manner, such as by using yeast or another fermentation agent such as bacteria, cyanobacteria, or other microorganisms. The fermentation agents can be naturally occurring, classically modified, or genetically modified to improve the fermentative process based on gains in efficiency or in product speciation. Fermentation of the hydrolyzed soluble compounds results in generation of oxygenates, $CO_2$, and potentially some insoluble by-products. These fermentation products are passed into a separator 145. At least a portion of the $CO_2$ is captured in a $CO_2$ storage tank 149, which can be used to generate a $CO_2$ stream 144 for use in growing additional algae. At least a portion of the insoluble by-product 148 is captured in a tank 147 for further processing. The by-product 148 can also potentially be added to animal or fish feed produced by the overall integrated process. Again, it is noted that practical limits on separations may result in oxygenate being retained in the insoluble by-product 148.

The oxygenate product from the fermentation 140 is then distilled 150 to generate a more concentrated oxygenate product in the aqueous environment. The resulting concentrated oxygenate stream can be stored 154 for later use. Alternatively, the concentrated oxygenate stream can be further processed to convert oxygenates formed during fermentation into other products before storage. The concentrated oxygenate stream, after optional further processing, can then be used as an input for other processes in the system. For example, a portion of the oxygenates can be used as an input stream 156 for oil recovery 120. Additionally or alternately, a portion of the oxygenates can be used as an input stream 157 for hydrolysis 130. Distillation 150 also generates additional water that can optionally be stored 152 prior to further use, such as recycling the water as an input stream 151 for an algae growth pond. Optionally, distillation 150 can be used to isolate other water-soluble products that are present in the aqueous environment. For example, the aqueous phase will typically include proteins, amino acids, or other non-fermentable materials that have value as input streams to other parts of the processing system. These materials can be isolated from the aqueous phase for use as nutrients or for other purposes.

In addition to generating oxygenates for use in the system and recycling water, the insoluble by-products generated in the system can also be processed to allow for nutrient recycling. The insoluble by-products 138 and 148 can be processed in various ways for nutrient recovery. One option is to use an acid wash 160 to extract nutrients such as nitrogen, phosphorous, and metals from at least a portion of the by-products. This results in a nutrient stream 162 that can optionally be stored 164 prior to delivery to an algae growth pond. Another option is to use an anaerobic digestor 170 to process at least a portion of the insoluble by-products. This can lead to a gas phase product 176 that may include methane and/or hydrogen. The gas phase product 176 can optionally be stored 177 for future use as a fuel, such as a fuel to generate heat for the system. Optionally, a second gas phase product 178 that includes $CO_2$ can also be generated. The $CO_2$-containing product 178 can be recycled to the algae growth system, stored for future use, or further processed in any other convenient manner. The gas phase product 176 and $CO_2$-containing product 178 can be separated 175 from a remaining nutrient stream 172. In FIG. 1, the gas phase product 176 and $CO_2$-containing product 178 are shown as separate streams emerging from separator 175 for convenience in describing the invention. However, gas phase product 176 and $CO_2$-containing product 178 can emerge from a separator 175 as a single stream that is then further processed to form separate streams 176 and 178. The nutrient stream 172 is optionally stored 174 prior to delivery to an algae growth pond.

Incorporation of Additional Biomass and Use of Oxygenates in Biodiesel Extraction Additional types of biomass are can be used to supplement the amount of desired products (such as distillate boiling range products) generated and/or to supplement the amount of fermentable material available in the system. In the example shown in FIG. 1, the only source of biological material is the algae from the algae growth pond. Any suitable type of algae-derived biomass will produce some product molecules, generate some residual biomass, and provide some nutrients and $CO_2$ for recycle to algae growth. However, for a typical algae, it is expected that some additional amounts of oxygenates, nutrients, and/or $CO_2$ will be required in order to maintain a continuous growth and harvesting cycle. For example, just from a mass balance perspective, the goal of an algae growth and processing system is to generate product molecules, such as molecules suitable for use in a fuel. Such molecules are extracted from the algae and leave the system for optional further processing. These molecules carry carbon out of the algae growth and processing system. To continue operation of the system, another source of carbon must be introduced.

The amount of oxygenates generated by a system can be another factor to consider. An algae strain that generates a desired amount of product material will not necessarily also generate a large amount of oxygenates after fermentation. One option could be to modify the processing conditions for an algae sample to balance extraction of product molecules with production of oxygenates. However, this type of balancing is likely to reduce the yield of molecules suitable for use as a fuel product, fuel blending product, or another type of product.

Another alternative is to add additional biomass to the processing system. Any convenient type of biomass may be added. One option is to add another type of biomass that also generates desirable product molecules. For example, an algae processing system could be located near a processing plant for a plant-based oil, such as soybean oil, rapeseed oil, or palm oil. In this type of example, a portion of the feed for the plant-based oil can be diverted to the algae processing system and co-processed with the algae. In addition to extracting plant oil, the remaining material from the plant material after processing will provide additional residual biomass for forming oxygenates or other solvents, generating $CO_2$, and/or generating nutrients. The additional $CO_2$ and/or nutrients recovered from the residual biomass from the plant oil processing could be used to increase the overall renewable character of the resulting biodiesel generated by the algae processing system. Other types of biomass that generate distillate boiling range material, such as seed type biomass, could also be co-processed.

Another option is to add biomass that is primarily intended for increasing the amount of fermentable material. In this type of option, the potentially fermentable content of biomass is used to provide additional material for oxygenate production and $CO_2$/nutrient generation. For example, corn is currently used as a raw material for producing ethanol as a renewable fuel. Rather than using the ethanol directly as a fuel, ethanol generated from corn can instead be used as a supplemental reagent for the extraction and processing of fuel or fuel product molecules generated from algae. The fuel or fuel product molecules (such as distillate boiling range molecules) can then be used as a fuel either directly or after additional processing or blending. By using algae as the primary source for generating a fuel while using corn to provide a supplemental reagent, the amount of corn needed per energy unit of fuel is greatly reduced. This is beneficial, as algae may be grown using land that is otherwise of low value, while corn is typically grown on arable land of high value. This provides an example of incorporating a reagent derived from a non-algal biomass source (oxygenates from processing corn) into a system for processing algae. Further integration between the processes can be achieved by using a fuel generated from the algae as a fuel source for the fermentation and/or distillations processes used to form oxygenates from the corn. One option is to use the product molecules harvested from the algae. A more attractive option is to use methane and/or hydrogen derived from anaerobic digestion of the algae as a fuel gas for oxygenate production.

More generally, locating an algae processing system in the vicinity of a plant for processing another type of biomass provides various synergies. Raw material or partially processed material from one type of processing plant may be passed to another plant. This can allow, for example, for provision of cellulosic material as an initial input, provision of oxygenates for facilitating algae processing, provision of additional $CO_2$ of a renewable nature to facilitate additional algae growth, exchange of fuel, heat energy, and/or mechanical energy between the processing systems, or any other convenient type of synergy between the processing plants. Having the plants in proximity also reduces the fossil fuel use needed to transport and process the various types of biomass.

Biomass typically contains three types of materials in substantial quantities. The three materials are cellulosic materials, hemicellulose, and lignin. Distillate boiling range molecules, oxygenates, and/or other product molecules are typically derived from cellulosic materials. Lignin is more difficult to process and is often burned for fuel value. Overall carbon efficiency can be increased by burning lignin for energy while capturing the resultant $CO_2$ for use as an input for algae growth. The five carbon sugars often produced from hemicelluloses are typically converted to ethanol at lower efficiency and with a significant remainder of unconverted material. The remainder of unconverted material can be burned to provide heat and $CO_2$. The heat can be used by other portions of the algae processing system, such as for distillation or hydrothermal processing. The $CO_2$ can be used as an input for further algae growth.

Figure 2:
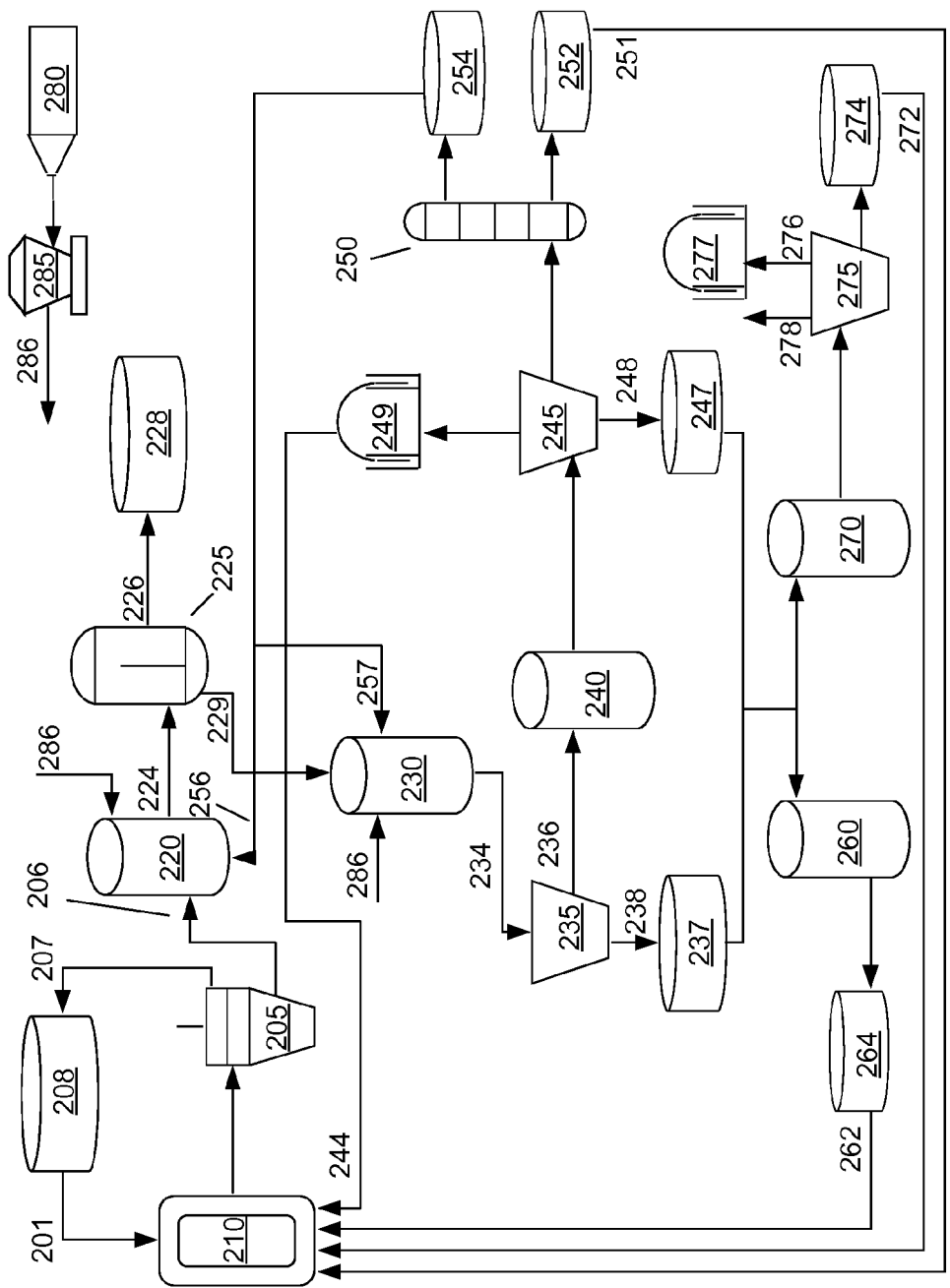
FIG. 2 depicts a reaction system suitable for performing a process according to another aspect of the invention.

FIG. 2 shows a system that includes various options for performing integrated product recovery. In the system shown in FIG. 2, two sources of biomass are used. One source of biomass is one or more algae pond(s) 210. The other source of biomass 280 can be any convenient biomass source other than an algae source such as algae pond(s) 210. This can include any of the non-algal biomass types mentioned above.

An initial process can be used to modify biomass from biomass source 280 prior to introduction of the biomass into an oil recovery process 220 or a hydrolysis process 230. A physical processor 285 can be used to convert the biomass into a particle size that is easier to use in subsequent processing. For example, plant biomass (such as cellulosic or lignocellulosic biomass) can be passed through a grinder, chopper, expeller, or other physical processor 285 in order to reduce and/or modify the particle size of the biomass. Such a physical process may also assist in separating oils from the residual material. If the oil recovery process 220 corresponds to a dry process, the physically modified biomass 286 can also be dried (not shown) to remove excess water. If hydrothermal processing or alcohol extraction is being used for oil recovery, such a drying step is optional, and may be unnecessary. The physically modified biomass 286 can also optionally be pelletized.

Other chemical and/or enzymatic methods can be used as an alternative to physical modification or in addition to physical modification. Chemical methods for modification of biomass use a chemical compound or mixture that breaks down the structural constituents of a cell and/or lyses the cells. Suitable chemicals include acids, (e.g hydrochloric acid, nitric acid, acetic acid, sulfuric acid, or phosphoric acid), bases (e.g. bleach, sodium hydroxide, potassium hydroxide, sodium carbonate, calcium carbonate, calcium hydroxide, solid catalysts, or ammonia), detergents, and hypotonic or hypertonic solutions. Enzymatic methods for modification of biomass use any enzyme or enzyme mixture that breaks down the structural constituents of a cell and/or lyses the cell.

FIG. 2 shows two options for how the physically modified biomass can be introduced into the algae processing portions of the system. One or both of the options may be used. One option is to introduce the physically modified biomass 286 into oil recovery process 220. A second option is to introduce the physically modified biomass 286 into hydrolysis process 230. To improve the readability of the figure, a fully connected line is not shown. Instead, just the output from physical processor 285 and the inputs to oil recovery 220 and hydrolysis 230 are shown.

In the option where physically modified biomass is introduced into oil recovery process 220, the physically modified biomass 286 is exposed to the same processing conditions used for extracting oil from algae in oil recovery process 220. Optionally, if oil recovery process 220 represents a batch or semi-batch type process, physically modified biomass 286 may be introduced into oil recovery process 220 either prior to or after algae and product stream 206 is introduced into the oil recovery process. After performing the oil recovery process 220, the effluent is passed into a separator 225. Stream 226 corresponding to at least a portion (and preferably a majority portion) of the one or more desired products) is passed to a storage tank 228 (or directly to a subsequent process), while the residual stream 229 is passed to hydrolyzer 230. The desired products can correspond to distillate boiling range molecules, molecules suitable for use in a fuel or a fuel blending product after optional further processing, or any other desired product. As in FIG. 1, other residual products may exit oil recovery process 220 in other streams that are not shown.

If the physically modified biomass 286 is introduced into oil recovery process 220, the desired product stream 226 will include product molecules based on both algae and product stream 206 and physically modified biomass 286. The introduction of the physically modified biomass 286 into the oil recovery process 220 will thus lead to an increase in the overall amount of oil recovered. Similarly, the residual stream 229 will include residual biomass corresponding to both residual algal material and residual non-algal biomass material. This means that more residual biomass is available for hydrolysis 230 and subsequent fermentation 240 to form $CO_2$ and oxygenates. This also results in more insoluble by-products 238 and 248 for use in generating nutrients for recycle to the algae growth pond 210. In the second option where physically modified biomass 286 is introduced directly to hydrolysis process 230, additional biomass will be introduced into hydrolysis process 230 without directly adding to the material in desired product stream 226.

In the system shown in FIG. 2, residual stream 229 is converted into one or more streams useful as inputs at other locations in the system. To begin this conversion, residual stream 229 is passed into a hydrolysis process 230 or another type of fermentation pretreatment. Hydrolysis process 230 can represent a chemical hydrolysis process, an enzymatic hydrolysis process, or a combination thereof. Preferably, hydrolysis process 230 can include the use of an alcohol or organic acid 257 that is provided by another process in the system. Hydrolysis process 230 generates a water soluble product of hydrolyzed polysaccharides and other hydrolyzed soluble compounds that are suitable for fermentation. Hydrolysis process 230 also generates an insoluble by-product. The outputs for hydrolysis process 230 are only representative, and additional water-soluble product and/or insoluble by-product streams may be generated.

The hydrolyzed product 234 from hydrolysis process 230 (or product from another fermentation pretreatment) is then passed into a separator 235. Separator 235 separates the hydrolyzed product into a water soluble product 236 and an insoluble by-product 238. The insoluble by-product can optionally be stored 237 prior to further processing. It is noted that the aqueous hydrolyzed product 236 may also include non-fermentable material. Similarly, a portion of fermentable material may be retained in insoluble by-product 238.

Water soluble product 236 is then passed into a fermenter 240 to convert the hydrolyzed soluble compounds (such as saccharides) into oxygenates, such as alcohols or organic acids. The fermentation is performed in any convenient manner, such as by using yeast or another fermentation agent such as bacteria, cyanobacteria, or other microorganisms. The fermentation agents can be naturally occurring, classically modified, or genetically modified to improve the fermentative process based on gains in efficiency or in product speciation. Fermentation of the hydrolyzed soluble compounds results in generation of oxygenates, $CO_2$, and potentially some insoluble by-products. These fermentation products are passed into a separator 245. At least a portion of the $CO_2$ is captured in a $CO_2$ storage tank 249, which can be used to generate a $CO_2$ stream 244 for use in growing additional algae. At least a portion of the insoluble by-product 248 is captured in a tank 247 for further processing. The by-product 248 can also potentially be added to animal or fish feed produced by the overall integrated process. Again, it is noted that practical limits on separations may result in oxygenates being retained in the insoluble by-product 248.

The oxygenate product from the fermentation 240 is then distilled 250 to increase the concentration of oxygenates in the aqueous environment. The resulting concentrated oxygenate stream can be stored 254 for later use. Alternatively, the concentrated oxygenate stream can be further processed to convert oxygenates formed during fermentation into other products before storage. The concentrated oxygenate stream, after optional further processing, can then be used as an input for other processes in the system. For example, a portion of the oxygenates can be used as an input stream 256 for oil recovery 220. Additionally or alternately, a portion of the oxygenates can be used as an input stream 257 for hydrolysis 230. Distillation 250 also generates additional water that can optionally be stored 252 prior to further use, such as recycling the water as an input stream 251 for an algae growth pond. Optionally, distillation 250 can be used to isolate other water-soluble products that are present in the aqueous environment such as proteins, amino acids, or other non-fermentable materials. These materials can be isolated from the aqueous phase for use as nutrients or for other purposes.

In addition to generating oxygenates for use in system 200 and recycling water, the insoluble by-products generated in system 200 can also be processed to allow for nutrient recycling. The insoluble by-products 238 and 248 can be processed in various ways for nutrient recovery. One option is to use an acid wash 260 to extract nutrients such a nitrogen, phosphorous, and metals from at least a portion of the by-products. This results in a nutrient stream 262 that can optionally be stored 264 prior to delivery to an algae growth pond. Another option is to use an anaerobic digester 270 to process at least a portion of the insoluble by-products. This can lead to a gas phase product 276 that may include methane and/or hydrogen. The gas phase product 276 can optionally be stored 277 for future use as a fuel, such as a fuel to generate heat for system 200. Optionally, a second gas phase product 278 that includes $CO_2$ can also be generated. The $CO_2$-containing product 278 can be recycled to the algae growth system, stored for future use, or further processed in any other convenient manner. The gas phase product 276 and $CO_2$-containing product 278 can be separated 275 from a remaining nutrient stream 272. In FIG. 2, the gas phase product 276 and $CO_2$-containing product 278 are shown as separate streams emerging from separator 275 for convenience in describing the invention. Gas phase product 276 and $CO_2$-containing product 278 can emerge from a separator 275 as a single stream that is then further processed to form separate streams 276 and 278. The nutrient stream 272 is optionally stored 274 prior to delivery to an algae growth pond.

Integrated Processing Including Gasification of Residual Solids

One method for increasing the renewable character of products generated from algae or other biological sources is to more fully capture and use all of the material present in a biomass sample. Extracting a distillate boiling range product, a fuel or fuel blending product, or another type of desired product from algae-derived biomass typically results in multiple output streams. At least one stream will correspond to the desired product(s) from the algae. The desired products may be used directly or after further additional processing. At least one other stream will correspond to residual biomass, such as algal husks, residual proteins, carbohydrates, and other material not suitable for use as a fuel product or conversion into a fuel product. The nature of this residual biomass will vary depending on the original source of the biomass and the type of extraction technique used for extracting the desired products. Increasing the ability to capture and recycle the residual biomass to other biological processes can reduce the amount of external inputs needed for creating products from algae or other biomass.

A gasification process can be used to facilitate recycling of residual biomass after oil recovery. More generally, gasification can be used to convert any type of biomass or residual biomass into small molecule products and a gasification residue. The small molecule products are typically suitable for a variety of purposes, while the gasification residue can be recycled as algae nutrients after additional processing. Gasification can process various co-feeds, such as feeds from both biological and fossil fuel sources. This can improve the gasification process by improving or optimizing the carbon to hydrogen ratio of the resulting gasification products, the fuel heating value of the resulting products, the syngas product composition, and/or other gasification process parameters. Additionally, any non-biological sources of fuel to the gasifier can produce lower greenhouse gas emissions by recycling gasifier products to the algae growth process.

In a gasification process, residual biomass (and/or other biomass) is exposed to a series of processing environments to convert the residual biomass into small molecule products and a gasification residue. Some of the small molecule products are formed by first converting the residual biomass to syngas and then using subsequent processing to form products from the syngas. Any convenient type of gasification procedure may be used. In an example of a gasification procedure, biomass is heated to about 100° C. to drive off excess water in the biomass sample. The steam generated from this initial process may be used later as part of a water gas shift reaction. Next, the temperature in the reaction environment is increased to about 200° C. to about 300° C. in an atmosphere with little or no oxygen. This drives off volatile organic molecules while converting carbon containing compounds to a carbon char. The creation of the carbon char may also create some low molecular weight hydrocarbons, such as methane. The carbon char is then combusted in an atmosphere with less than a stoichiometric amount of oxygen. The combustion temperature can be up to about 1200° C. (2200° F.) or greater. This converts the carbon char to CO and $CO_2$. Optionally, if steam is present in the reaction environment, the carbon can react directly with the steam to form $H_2$ and CO. The CO created during combustion can also undergo the water gas shift reaction to form $H_2$ and additional $CO_2$. In another example, gasification can be performed using a single-stage entrained flow reaction system at temperatures of up to about 2000° C. (3600° F.) or higher. There are a variety of fuel pretreatment methods that may also be employed including torrefaction and hydrothermal treatment. The choice of treatment will typically depend on the gasification technology employed and the presence or absence of any co-feed to the gasifier. Biomass may be fed into a gasifier as a finely divided solid, a pre-processed liquid, a partially volatile material, or any combination of these.

Additional heteroatoms in the biomass are also converted to other forms during gasification. For example, nitrogen present in the biomass will typically be converted to $NH_3$ and/or $N_2$ during gasification. Other common nutrients in biomass, such as phosphorous and trace metals, do not form product that is stable as a gas phase at ambient temperatures. Instead, phosphorous and trace metals present in biomass typically are incorporated into a solid slag or gasification residue.

The various products from gasification can be separated into a few product groupings. The $NH_3$ and $CO_2$ generated during gasification can be separated from the remaining gas phase products using conventional methods. The $NH_3$ and $CO_2$ are suitable for use as nutrients for additional algae growth. Alternatively, the $NH_3$ may be incorporated into a fertilizer for growth of other types of biomass. If $N_2$ is generated during gasification and separated from other gas phase products, the $N_2$ can be converted into additional $NH_3$ using an ammonia synthesis plant. An ammonia synthesis plant facilitates generation of ammonia via the reaction $3H_2 + N_2 => 2NH_3$.

The $H_2$ and CO generated during gasification can also be used in a variety of ways. One option is to use a portion of the $H_2$ and CO as a fuel gas. Any volatile carbon compounds such as $CH_4$ that are generated in the gasification environment can also be used as part of the fuel gas.

Another option is to convert a portion of the CO and $H_2$ (sometimes referred to as syngas) into one or more types of organic molecules. For example, CO and $H_2$ can be used as an input stream for methanol production. Any convenient method for conversion/synthesis of CO and $H_2$ into methanol may be used. Using CO and $H_2$ for methanol production provides another opportunity for further process integration. Methanol could be used as a reagent for facilitating hydrothermal processing of biomass for oil extraction. Alternatively, methanol can be used as part of a process for forming fatty acid methyl esters (FAME) from a biomass-derived product. Some conventional refinery processes are already adapted to use FAME as part of a feed for diesel fuel production. Using methanol to convert distillate boiling range compounds into FAME provides a way to create a product that can be used directly with existing technologies.

Still another option is to use the CO and $H_2$ as a feed for direct fermentation of ethanol. A variety of microorganisms can directly convert CO and $H_2$ to ethanol. The ethanol can then be used as a fuel, as a solvent in extraction of algae oils, or as a solvent in hydrothermal processing of algae, or as a reactant to form other products.

Yet another option is to use a portion of the CO and $H_2$ as feed for a Fischer-Tropsch synthesis reaction. The Fischer-Tropsch reaction is a conventionally known process for converting CO and $H_2$ in the presence of a catalyst into alkanes. Conventional uses for Fischer-Tropsch products include creating molecules suitable for use in fuels and creating building block molecules for creating polymers or other larger compounds. The products generated by a Fischer-Tropsch process are dependent on the type of catalyst and the other reaction conditions selected. Any convenient type of Fischer-Tropsch process may be used, including those based on iron ("high-temperature Fischer-Tropsch") or cobalt ("low-temperature Fischer-Tropsch") catalysts. A Fischer-Tropsch process will typically produce a product that is mostly paraffinic in nature. The product is suitable for use directly or as blending stock as a wax, distillate or naphtha, or can be into one of these products through hydroprocessing steps such as hydroisomerization or hydrocracking. A Fischer-Tropsch process will also typically generate one or more residual streams of light gases that are suitable as fuel for heating or producing electricity, as well as residual $CO_2$ which is suitable for use as a feed for algae growth. Additionally, the Fischer-Tropsch process is exothermic and can provide energy (such as via heat exchange) to any of the individual process steps mentioned herein, such as heating, drying or pretreatment of biomass prior to gasification.

By using a combination of gasification and a Fischer-Tropsch reactor, residual biomass can be converted into a variety of potential products. The potential products can be either direct products, or products for further processing such as polymer building blocks. In addition to the main alkane product, the Fischer-Tropsch reaction will generate a variety of alkenes, alcohols, and other oxygenates. The amount and type of these additional by-products will vary depending on the catalyst and the reaction conditions. The alcohols and other oxygenates from Fischer-Tropsch processing can be recovered for use as oxygenates in any of the previously described manners, including use as a reagent for hydrothermal processing of biomass.

Figure 3:
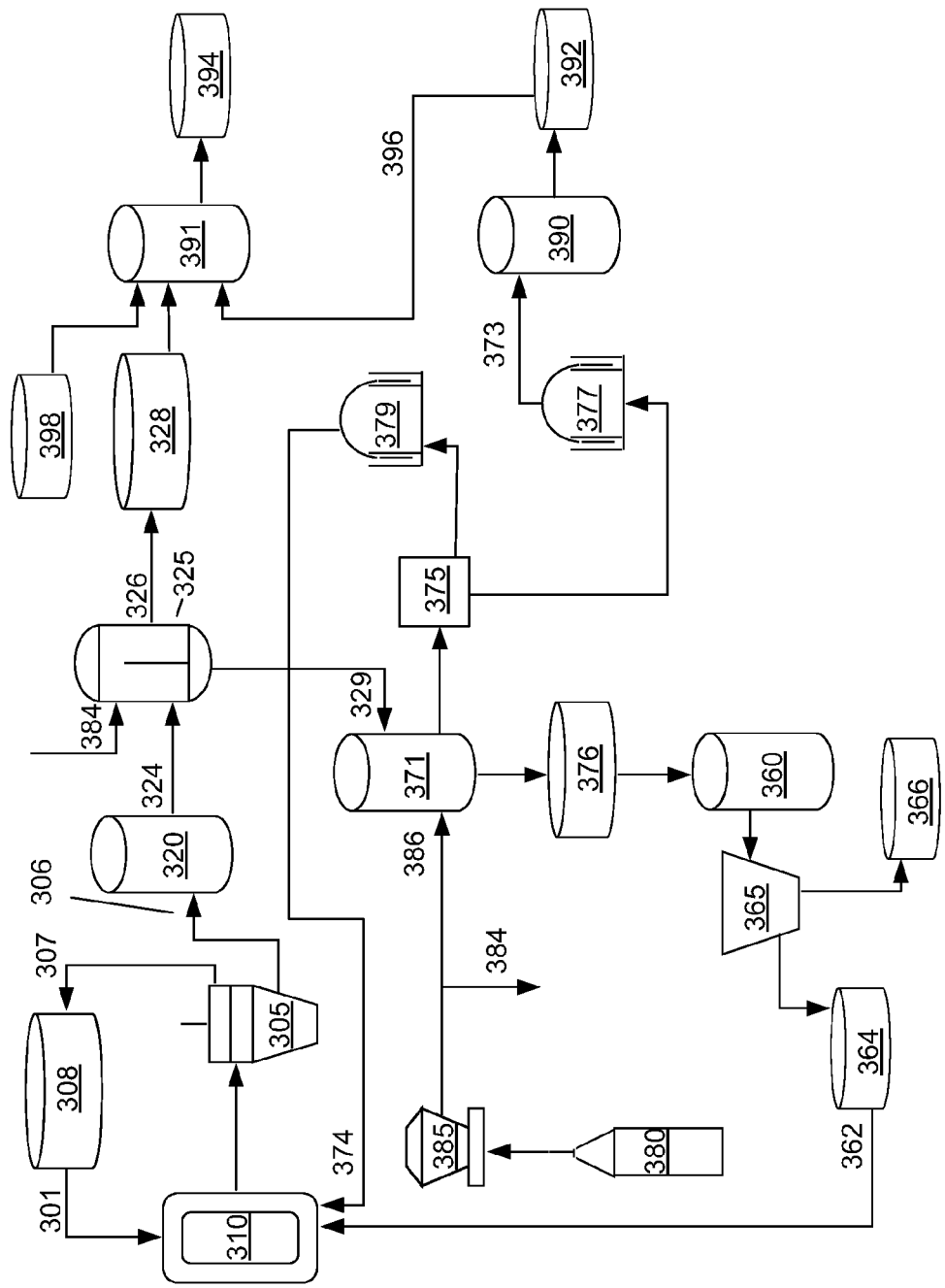
FIG. 3 depicts a reaction system suitable for performing a process according to another aspect of the invention.

FIG. 3 shows a system that includes various options for performing integrated recovery of desired product(s) from an algae source. A system such as shown in FIG. 3 uses the residual biomass from product extraction as a feed for gasification. The outputs from gasification can be integrated for further use in a variety of ways.

In FIG. 3, one or more algae growth ponds 310 allow for growth of algae and formation of desired products. Growth pond 310 receives a variety of inputs. FIG. 3 shows inputs that are generated by other portions of the system for processing the algae. These inputs include water stream 301, nutrient stream 362, and stream 374 that contains $CO_2$ and/or $NH_3$. All of these streams are optional, depending on the configuration of the algae growth and product recovery system. If desired, the algae growth pond can be optionally supplied with additional water, nutrients, and/or $CO_2$ from external sources. Examples of external sources include crop residues not directly involved in biofuel production or residual biomass not used in animal feed production.

When it is desired to process the algae in a pond for product extraction, the algae is initially dewatered, such as by using a centrifuge 305. Centrifuge 305 generates an algae stream and a product stream 306 with a reduced water content and a side water stream 307. Side water stream 307 can be stored in a water storage tank 308 until growth pond 310 is ready to receive additional water as water stream 301. Alternatively, side water stream 307 can be returned directly to a growth pond, such as growth pond 310. It is noted that algae and product stream 306 may only contain a portion of the algae and product entering centrifuge 305, as some algae and product may be returned to the growth pond 310 with side water stream 307.

The algae and product stream 306 with reduced water content is then exposed to processing conditions for extracting the desired product(s) in an oil recovery process 320. The desired products can correspond to distillate boiling range molecules, molecules suitable for use in a fuel or fuel blending product after optional further processing, or other types of product molecules.

In some cases, additional biomass 380 is introduced into oil recovery process 320 for oil extraction. Examples of suitable oil recovery processes 320 include hydrothermal processing and alcohol extraction. Typically, an initial process can be used to modify biomass from biomass source 380 prior to introduction of the biomass into an oil recovery process 320 (or a hydrolysis process 330). A physical processor 385 can be used to convert the biomass into a particle size that is easier to use in subsequent processing. For example, plant biomass (such as cellulosic or lignocellulosic biomass) can be passed through a grinder, chopper, expeller, or other physical processor 385 in order to reduce and/or modify the particle size of the biomass. Such a physical process may also assist in separating oils from the residual material. In FIG. 3, non-algal biomass can optionally be added to oil recovery process 320 (via physically modified biomass stream 384) or to gasification process 371 (via physically modified biomass stream 386). If the oil recovery process 320 corresponds to a dry process, the physically modified biomass 384 can also be dried (not shown) to remove excess water. If hydrothermal processing or alcohol extraction is being used for oil recovery, such a drying step is optional, and may be unnecessary. The physically modified biomass 384 can also optionally be pelletized. Note that in FIG. 3, stream 384 is not shown as a continuous line for convenience in viewing the figure.

Optionally, alcohol and/or organic acids for use in oil recovery process 320 are provided as an input stream that is generated by a later process within system, such as methanol synthesis 390. Alternatively, alcohols and/or organic acids for use in oil recovery process 320 can be provided from another biomass processing system, such as a system for converting corn or sugar cane into oxygenates. The residual biomass after fermentation of the corn or sugar cane can be used as a biomass input 380 for gasification.

After oil recovery process 320, the effluent 324 is passed to a separator 325. A portion of effluent 324 is separated out to form a stream 326. Stream 326 includes at least a portion (and preferably at least a majority) of the desired product(s). In FIG. 3, stream 326 is passed into a storage tank 328 to be held for further processing. Examples of further processing include further refinement, purification, or other modification of the product. FIG. 3 shows an example of further processing of distillate boiling range product stream 326 in the form of FAME synthesis process 391. In the system shown in FIG. 3, at least some of the distillate boiling range product in stream 326 corresponds to triacylglycerols and/or corresponds to molecules that can be converted into triacylglycerols. The products in stream 326 can be combined with other sources of triacylglycerols 398 as a feed for FAME synthesis process 391. The triacylglycerols are combined with methanol 396 to form a FAME product that is stored 394 for future use or processing.

The remaining portion of effluent 324 exits separator 325 as a residual stream 329. This residual stream may include a variety of materials, including algal husks and other excess solids that remain after recovery of the desired product. Residual stream 329 may also include a portion of the distillate boiling range product due to practical limitations in performing the separation. Note that residual stream 329 may correspond to only a portion of the residual products from oil recovery process 320. Other residual products may exit oil recovery process 320 in other streams that are not shown.

Residual stream 329 can be converted into one or more streams useful as inputs at other locations in the system. To begin this conversion, residual stream 329 is passed into a gasifier 371. Additional biomass 380 can also introduced into the gasifier via stream 386. The additional biomass can be raw biomass, or the additional biomass can be previously processed for product extraction. Examples of additional biomass 380 include brewer's grain or other biomass that has already been processed by fermentation to generate oxygenates, or other residual biomass such as residual biomass from an oil recovery process. Optionally, the additional biomass is pulverized 385 prior to introduction of the biomass stream 386 into the gasifier. Any convenient type of gasifier can be used, such as a fixed bed gasifier, a fluidized bed gasifier, or an entrained flow gasifier. Gasifier 371 generates a gas phase product that is passed to a gas phase separator 375. Gasifier 371 also generates a solid by-product, which is passed to a solid by-product storage 376. The outputs shown for gasifier 371 are only representative, and other gas phase or solid by-product streams may also be generated.

In the system shown in FIG. 3, gas phase separator 375 separates the gas phase product from the gasifier into at least two streams. A first stream can include one or more of $CO_2$ and $NH_3$. The $CO_2$ and $NH_3$ are separated out by any convenient method, such as using a water wash for the $NH_3$ and/or an amine wash for the $CO_2$. In the system shown in FIG. 3, the $CO_2$ and/or $NH_3$ are stored in gas storage 379 for further use, such as use as nutrients 374 for algae growth. A second stream can include one or more of $H_2$ and CO. In the system shown in FIG. 3, the $H_2$ and CO are stored in gas storage 377 for further use. FIG. 3 shows use of an $H_2$ and CO feed stream 373 as an input for methanol synthesis 390. The methanol generated from methanol synthesis 390 is optionally stored 392 for further use. For example, the stored methanol can be used as an input 396 for FAME synthesis 391. It is noted that a water gas shift process may optionally be used to modify the ratio of CO, $CO_2$, and $H_2$ in the output stream from gasifier 371. Also, the separation in gas phase separator 375 may be incomplete, so that portions of $H_2$ and CO are included in the stream containing $CO_2$ and $NH_3$, and vice versa.

As an alternative to the configuration shown in FIG. 3, a different type of separation may be performed on the gas phase output from gasifier 371. For example, the gas phase output can be purified to remove, for example, $NH_3$ from the gas phase output. The remaining gas phase stream can then be used for the $H_2$ and CO content of the stream. In this option, the $CO_2$ present in the gas phase output from the gasifier acts as a diluent in the syngas stream. Many uses for syngas, such as methanol synthesis, Fischer-Tropsch synthesis, or use as a fuel gas, can tolerate the presence of some excess $CO_2$ in a syngas input stream. Note that the $NH_3$ removed from the gas phase output can optionally be recycled as a nutrient for algae growth and/or production of fertilizer for other biomass growth.

The optionally stored solid by-product 376 from gasifier 371 is then passed into an acid wash 360. Acid wash 360 assists with converting the solid by-product from gasifier 371 into a form suitable for use as a nutrient for algae growth. The effluent from acid wash 360 is passed into a separator 365. The water soluble portion of the effluent from acid wash 360 is separated out and optionally stored 364 prior to use as a nutrient feed 362. The nutrient feed 362 will typically include phosphorous and trace metals found in biomass. An insoluble by-product 366 is also separated out.

Reciprocal Integration of Algae Processing and Non-Algal Biomass Processing

Still another type of process integration suitable for use with various aspects of the invention is to allow energy and/or products to be transferred in both directions between an algae processing system and a non-algae biomass processing system. For example, corn can be used as a raw material for producing ethanol or another oxygenate. Rather than using ethanol as a fuel, the ethanol can be used as a reagent for extraction of desired product(s) from algae. This provides an example of generating a reagent from a non-algae biomass source (oxygenates from corn) for use in generating a desired product from algae. Further process integration can be achieved by using a product from processing of the algae as a reagent or energy source for making oxygenates from corn. For example, the fermentation and distillation processes involved in making oxygenates from a plant based material require temperatures above ambient. A product from processing the algae can serve as at least a portion of the fuel for generating heat for the fermentation and/or distillation processes. One choice is to use distillate boiling range products or a corresponding finished fuel product as a fuel for ethanol processing. A potentially more attractive option is to provide a methane or hydrogen stream as fuel. Anaerobic digestion of residual biomass during algae processing typically generates methane and/or hydrogen as a digestion product. This methane and/or hydrogen product can be transferred to the corn processing plant for use as a fuel. At least one compound produced from a non-algal biomass source is then used as a reagent for producing desired products from algae. Additionally, at least one product or energy output from the algae processing system is used as an input for the processing of non-algal biomass into a fuel or chemical product. In the above example, one portion of the ethanol derived from corn can be used as a fuel while a second portion is provided to the algae processing system. Multiple algae and/or non-algae processing systems can be co-located, so that the non-algal biomass processing system that delivers the reagent to the algae processing system is different from the non-algal biomass processing system that receives a product or energy input from the algae processing system. A portion of low-level heat can be transferred back into the algae pond to maintain optimal temperatures for growth. Typically the low level heat source will have a temperature below 300° C., more commonly below 200° C., and more commonly below 100° C. Transfer of low-level heat is particularly beneficial in climates where average temperatures are colder than optimal growth temperatures.

The system shown in FIG. 3 shows a system for extracting products from algae-derived biomass followed by gasification of the algae-derived biomass residue to create additional material suitable for further use or recycle. Non-algal biomass can be added to the system in FIG. 3 at various points, but such integration with outside biomass sources and/or processes is optional. In the example shown in FIG. 3, at least a portion of the desired products (such as fuel or fuel blending products) extracted from the algae feed correspond to molecules suitable for use in making FAME. However, some types of algae will make product molecules that are not readily converted into FAME or another type of fatty acid methyl ester. Additionally or alternately, it may be desirable to use the extracted products from the algae feed for another purpose while making FAME based on a different biomass source.

Figure 4:
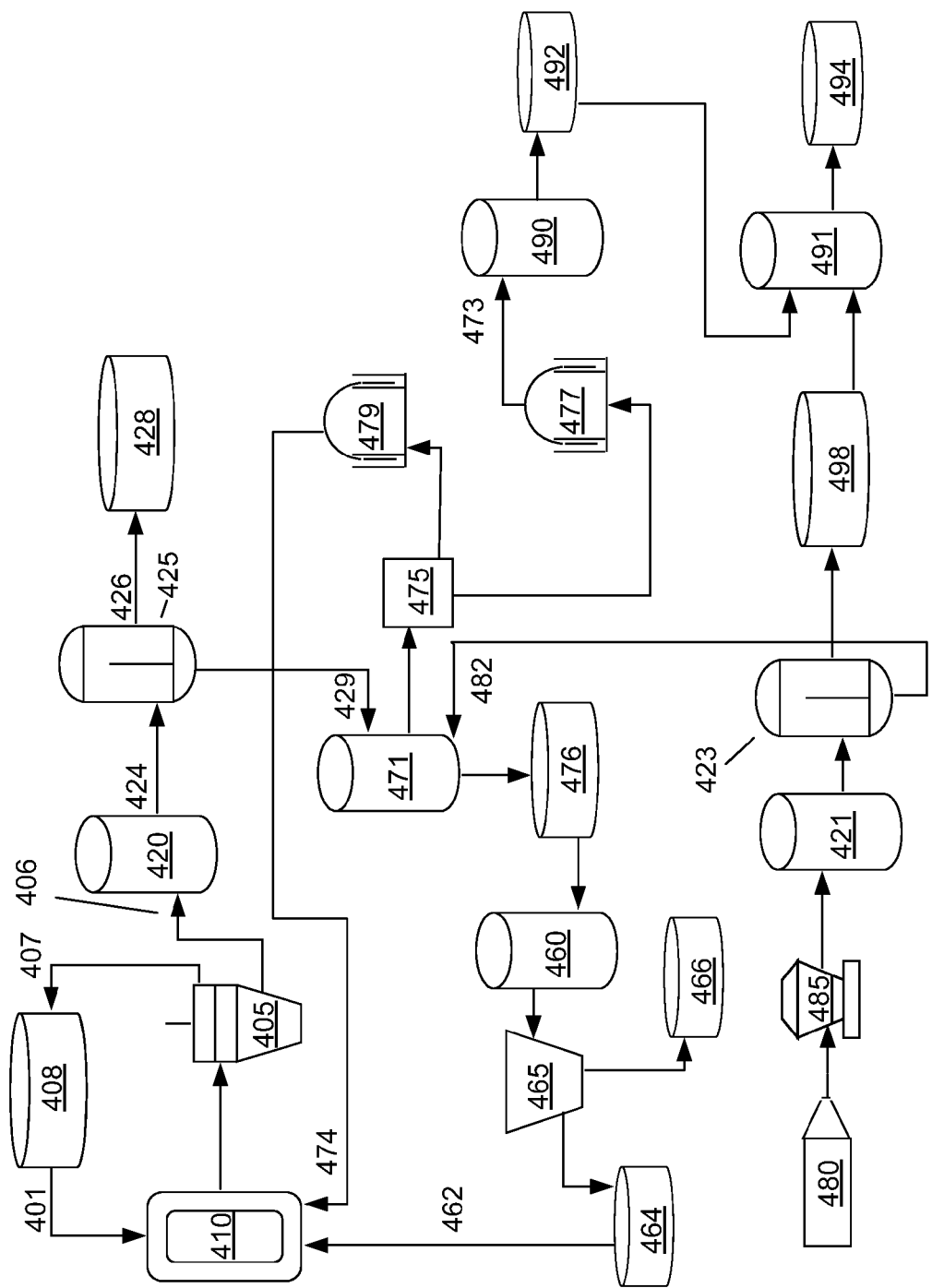
FIG. 4 depicts a reaction system suitable for performing a process according to another aspect of the invention.

FIG. 4 shows an example of an algae processing system that includes greater integration with processing of multiple types of biomass. The multiple types of biomass for FIG. 4 can be more than one type of algae source, or the multiple types of biomass may include at least one algae-derived biomass source and at least one non-algal biomass source. In FIG. 4, an algae pond 410 or other source of algae growth is used to provide a feed of algae-derived biomass. The algae feed is at least partially dewatered 405. The excess water 407 can be recycled to a holding tank 408 for eventual use to replenish algae growth pond (or other growth environment) 480. One or more desired products are then extracted 420 from the dewatered algae feed 406. At least a portion of the desired product(s) are separated out 425 from the oil recovery effluent 424 to form a desired product stream 426. This desired product stream 426 can be optionally stored 428 prior to further use. In the system shown in FIG. 4, the product stream 426 is not used to make FAME as part of the system shown in FIG. 4. This could be for any of a variety of reasons. The product stream 426 may have a low content of triacylglycerols and/or other molecules suitable for eventual conversion into FAME. Another possibility is that product stream 426 may have a higher value as a feed for producing another type of product. Still another option is that product stream 426 will be used for creating fatty acid alkyl esters, but it is more convenient to use product stream 426 in another processing plant or a different area of the same processing plant.

A residual stream 429 remaining after extraction 420 of products from the algae-derived biomass is used as a feed for gasifier 471. In FIG. 4, gasifier 471 also receives biomass for gasification via feed 482. Gasifier 471 can generate a variety of output flows. A portion of the output corresponds to a gas phase output. The gas phase output can be separated 475 into at least two streams. One output can include $NH_3$ and/or $CO_2$, which are optionally stored 479 prior to further use. The $NH_3$ and/or $CO_2$ can then be used as algae nutrients 474 for algae source 410, as fertilizer for another biomass growth process (not shown), or for another convenient purpose. The nutrient stream 474 may undergo further processing prior to use as nutrients or a fertilizer. Another output can include $H_2$ and CO (syngas) which are optionally stored 477 prior to use as an input 473 for methanol synthesis 490. Optionally, a water gas shift reaction can modify the ratios of $H_2$, CO, and $CO_2$ in the output streams 474 and 473 generated by gasifier 471.

As an alternative to the configuration shown in FIG. 4, a different type of separation may be performed on the gas phase output from gasifier 471. For example, the gas phase output can be purified to remove, for example, $NH_3$ from the gas phase output. The remaining gas phase stream can then be used for the $H_2$ and CO content of the stream. In this option, the $CO_2$ present in the gas phase output from the gasifier acts as a diluent in the syngas stream. Many uses for syngas, such as methanol synthesis, Fischer-Tropsch synthesis, or use as a fuel gas, can tolerate the presence of some excess $CO_2$ in a syngas input stream.

Another output stream from gasifier 471 is a solid by-product output stream, which is optionally stored 476. An acid wash 460 is an example of how the solid by-product output can be further processed to convert at least a portion of the solid by-product into nutrients suitable for facilitating algae growth. Acid wash 460 assists with converting the solid by-product from gasifier 471 into a form suitable for use as a nutrient for algae growth. The effluent from acid wash 460 is passed into a separator 465. The water soluble portion of the effluent from acid wash 460 is separated out and optionally stored 464 prior to use as a nutrient feed 462. The nutrient feed 462 will typically include phosphorous and trace metals found in biomass. An insoluble by-product 466 is also separated out The system shown in FIG. 4 also includes a second source of biomass 480. The second biomass source 480 can be an algal or non-algal biomass source. In FIG. 4, the biomass in biomass source 480 generates product molecules suitable for use in forming fatty acid alkyl esters. The biomass in source 480 can correspond to a seed or vegetable oil biomass source, such as rapeseed or soybeans. Alternatively, biomass source 480 can be an algae growth pond for growing algae that are the same or different from the algae in algae source 410. Biomass source 480 is used to provide a feed for oil recovery process 421. Optionally, the feed from biomass source 480 may be dewatered (not shown), pulverized or physically modified 485, or otherwise pre-processed to improve the suitability of the feed for oil recovery process 421. Oil recovery process 421 can be any convenient type of process for extracting distillate boiling range products, such as hydrothermal processing or alcohol extraction. The output flow from oil recovery process 421 is separated 423 to form at least a product stream and a residual biomass stream. The residual biomass stream 482 is passed into gasifier 471 for gasification. The product stream is optionally stored 498 prior to further processing. In FIG. 4, the product stream 498 includes molecules, such as triacylglycerols, suitable for use in forming fatty acid alkyl esters. At least a portion of product stream 498 is used in combination with methanol feed 492 to make FAME 491. The FAME product may optionally be stored 494 prior to further use.

The configuration shown in FIG. 4 provides another example of integration of multiple biomass processing systems. The process flow for processing of algae source 410 results in generation of methanol. The methanol is integrated into the process flow for processing of second biomass source 480. Recovering oil from second biomass source 480 provides a residual stream 482 that is delivered to gasifier 471. This increases the amount of biomass available for gasification, which reduces the amount of additional $CO_2$ and/or other nutrients required for sustaining algae source 410.

Integration of Fischer-Tropsch Processes with Biomass Processing

Figure 5:
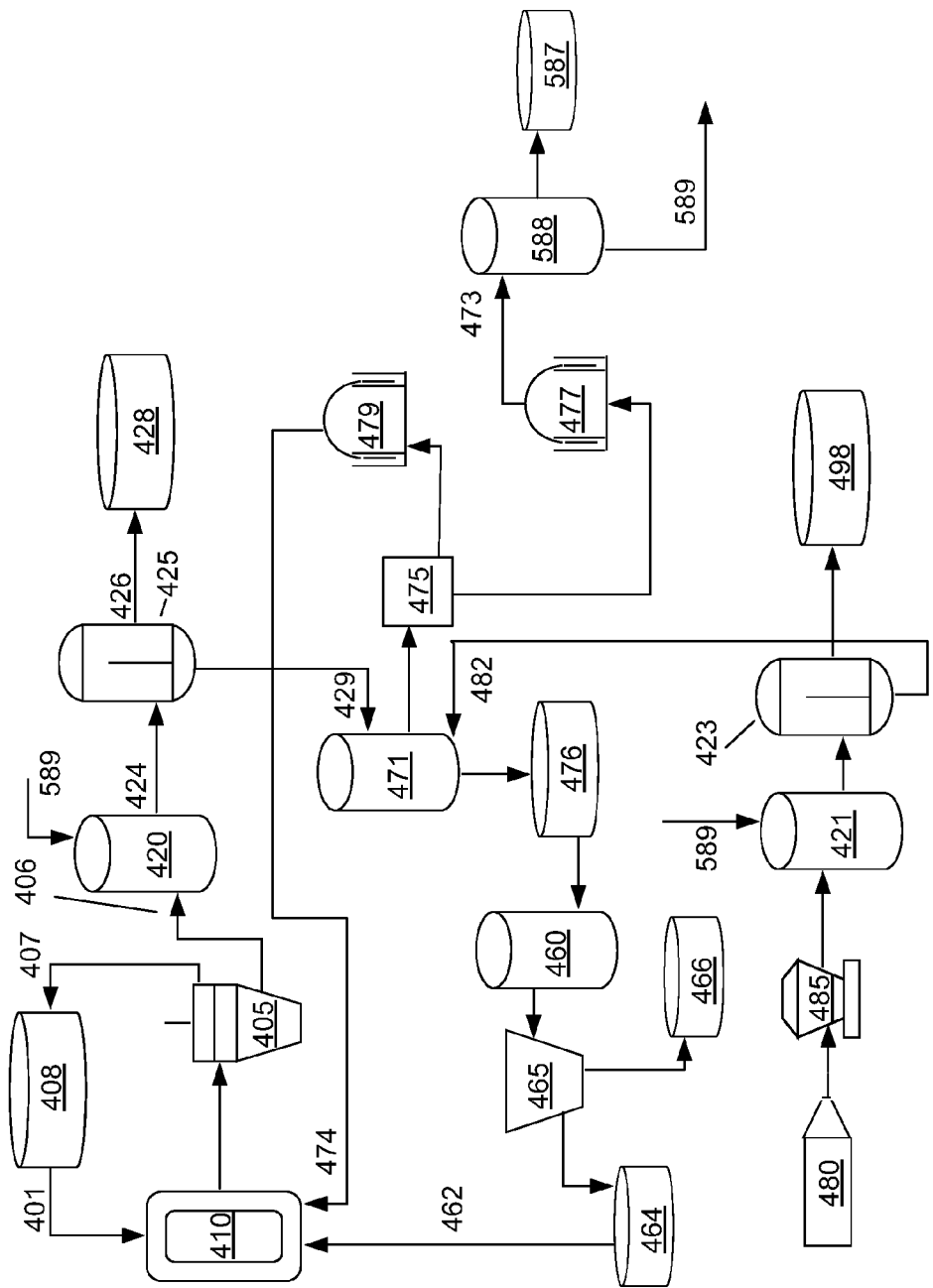
FIG. 5 depicts a reaction system suitable for performing a process according to another aspect of the invention.

A syngas stream ($H_2$ and CO) generated by gasification of biomass can be used as a feed for processes other than methanol synthesis. FIG. 5 provides an example of using at least a portion of the syngas output stream for Fischer-Tropsch synthesis of alkanes.

For convenience in explaining the use of Fischer-Tropsch processing, the system shown in FIG. 5 has a similar configuration to FIG. 4. However, any other convenient configuration for oil extraction from algae biomass with gasification of a residual stream may also be used. In FIG. 5, gasifier 471 produces at least one gas phase output stream. The gas phase output stream is separated 475 to form a stream 474 containing at least $NH_3$ and/or $CO_2$, as described above, and a stream 473 containing at least $H_2$ and CO. The output stream 473 containing $H_2$ and CO is used as a feed for a Fischer-Tropsch synthesis process 588. Fischer-Tropsch process 588 produces at least two output streams. One output stream includes mostly paraffins 587, which are an intended product of a Fischer-Tropsch reaction. The use of paraffin-rich stream 587 depends on the type of molecular weight distribution generated by the Fischer-Tropsch reaction and the intended use. The material can be converted into a variety of fuel or fuel blending products either by use of specific cuts or with further processing. Another output stream 589 contains a mixture of oxygenates, such as alcohols and/or organic acids that primarily contain three carbon atoms or less. Such oxygenates are suitable for use, for example, in hydrothermal processing or other oil recovery processes. In FIG. 5, the potential use of the oxygenates in output stream 589 is represented by showing the optional use of 589 as an input in oil recovery processes 420 and/or 421. Prior to using the oxygenates from stream 589 in an oil recovery process (or another process), the concentration of the oxygenates can optionally be increased using a separation or distillation process. As noted above, a typical Fischer-Tropsch process will also produce a variety useful by-products. Because a Fischer-Tropsch process is exothermic, heat from the Fischer-Tropsch process 588 can be used to provide energy for another nearby process. Fischer-Tropsch process 588 will typically also make residual light gases which are suitable for use as a fuel gas for generating energy. Additionally, Fischer-Tropsch process 588 will give off residual $CO_2$ which can be used as a nutrient for algae growth, such as by providing the $CO_2$ to algae source 410.

Algae Growth and Harvesting

The algae used to provide biological matter for production of fuels or other products and for use in accordance with various aspects of the present invention may be grown in any convenient manner. Typical algae growth environments include ponds and photobioreactors. Although any size pond may be used, the inventive structures and methods are generally used with ponds having a size of at least about 0.01 acres, including ponds of at least about 1 acre, at least about 10 acres and at least about 20 acres. In this discussion, references will be made to growth of algae in a pond. This is not intended to restrict the invention to use of a single pond for algae growth and harvesting or to limit the invention to only open systems. Instead, any convenient number of ponds, photobioreactors, or other growth environments may be used. Due to the batch or semi-batch nature of various methods for processing algae to form hydrocarbon products, having multiple algae growth ponds or photobioreactors may provide an advantage. For example, the algae in a first pond can be harvested for processing to extract hydrocarbons while algae in one or more other ponds continue with growth and/or oil production.

Any convenient pond or reactor structure can be used in the invention. One example of a suitable pond is a raceway pond. Raceway ponds are generally preferred due to their relatively uniform fluid dynamics. The intermediate divider for the tracks in a raceway pond also provides a suitable support for a pond cover. Other choices include circular ponds, tubular photobioreactors, and flat panel photobioreactors.

One or more algae ponds are used to grow at least a portion of the algae. An algae pond generally includes a mechanism for inducing a flow into the pond, such as a paddlewheel. A paddlewheel provides a defined current within the pond, allowing for control of a bulk flow rate of the water in the pond. Additional modifications to the flow pattern within a pond can be made by allowing the cover to come into contact with the water surface at various locations, by including active and/or passive flow modification structures within the pond, or by other convenient methods. Alternative methods for introducing flow into the pond include simple gravity flow or pumping of water by conventional methods. In a photobioreactor or other closed system, some form of pumping mechanism is often used to introduce flow into the system.

An algae growth pond can have any convenient width. In this discussion, the width of a raceway pond that includes a central dividing wall is defined as the width from an edge of the pond to the divider. Note that the width of a pond structure can, but preferably does not, vary along the length of a pond. Typically the length to width ratio of a pond is between 2 and 50, more commonly between 5 and 15. For ponds having a surface area greater than 1 acre, a length to width ratio of 10 to 15 is common. For example, a 1 acre pond with a length to width ratio of 15 corresponds to a pond with a width of about 54 feet. Larger length to width ratios require more pumping force, such as larger paddlewheels or multiple paddlewheels, while wider ponds are more difficult to mix.

The pond can have any convenient depth. Although not preferred, the depth can also vary along the length and/or width of the pond. Due to absorption of light by algae, in a typical pond only the first few centimeters of the pond will experience a light intensity that is at least 10% of the light intensity incident on the pond surface. Depending on the density of the algae and the concentration of chlorophyll in the cells, the depth of water in the pond experiencing more than 10% of the incident light intensity can be 20 cm or less, or 10 cm or less, or 5 cm or less, or 2 cm or less, or 1 cm or less. As a result, algae below a given depth in a pond will experience little or no light intensity. Having algae experience time periods of little or no light intensity is a condition that occurs naturally in ponds, and the presence or absence and duration of such time periods impacts the photosynthetic efficiency of algae. In general, algae grow faster when the algae are exposed to intermittent light as opposed to continuous light. The optimum depth and mixing requirements of the pond are dependent on the algae species and the corresponding efficiency of the algae for capturing light intensity. For most species, continuous direct sunlight result in a solar radiation level greater than the maximum level that can be used by the algae. This leads to excess light intensity that is wasted primarily as absorbed heat.

In order to provide improved control over the growth and/or lipid production of algae in a pond, it can be beneficial to limit the depth of the pond so that algae in a lower depth (darker) portion of a pond can be returned to the portions of the pond closer to the surface on a desired time scale. In addition, it is easier to maintain a desired amount of mixing or turbulence in a shallow pond, allowing for rapid exchange of algae from darker to lighter regions. As noted above, exposing algae to intermittent light intensity rather than continuous light intensity will typically enhance the growth rate of the algae. For example, based on the operation of the paddlewheel or other device for inducing a flow, water in the pond can have an average circuit time around the pond on the order of hours. In order to achieve intermittent exposure of algae to light intensity, during a full circuit of the pond, it is generally desirable for algae to spend an average of about 10% to about 50% of the pond circuit time in a region having greater than about 10% of the incident light intensity. Alternatively, the average amount of time algae experience at least 10% of the incident light intensity can be at least about 15% of the circuit time, or at least about 20%, or at least about 25%, or about 50% or less, or about 40% or less, or about 30% or less. The preferred amount of time for algae to be exposed to greater than about 10% of the incident light intensity is dependent on a variety of factors, such as the type of algae and the desired balance between algae growth and algae oil production. For example, some algae may have a high rate of photon absorption when exposed to light, but may also need longer periods away from sunlight to achieve efficient growth and/or oil production. Such algae may prefer decreasing amounts of time with exposure to greater than 10% of incident light intensity. For algae that have little or no drop in efficiency when exposed to additional light, the higher amounts of time with exposure to greater than 10% of incident light intensity may be preferred. In a photobioreactor or other system where light is provided by an artificial source, exposure to desired amounts of light intensity can be controlled by managing the duty cycle of the light source.

For a well-mixed pond, one way of controlling the amount of incident light the algae is exposed to is based on a combination of the algae density in the pond and the depth of the pond. At a given algae density, increasing the depth of the pond will decrease the amount of time algae is exposed to at least 10% of the incident light. This is due to a greater percentage of the pond being far from the surface, and therefore a greater percentage of the pond volume will be below the depth where light is attenuated to less than 10%. The amount of light attenuation is also dependent on the type of algae and the algae concentration. Different algae have different concentrations of chlorophyll, and thus different efficiencies at capturing versus transmitting light. To achieve a desired amount of light attenuation, the depth of the pond can be selected to be about 100 cm or less, or about 75 cm or less. More typical pond depths will be about 50 cm or less, or about 35 cm or less, or about 30 cm or less. Additionally or alternately, the depth of the pond can be at least about 5 cm, or at least about 10 cm, or at least about 20 cm.

Optionally, a pond may include a partial or complete cover structure. A cover structure reduces or prevents interaction between a pond and the surrounding environment. A cover structure reduces or prevents introduction of outside material, such as rainwater or microorganisms native to the pond location. A cover structure also reduces or prevents evaporative water loss, and may assist in retaining $CO_2$ within a growth pond for consumption by algae. Suitable cover structures include surface covers located at or near the surface of the water in a pond as well as greenhouse type structures that (partially) enclose a substantial volume of air above the surface of a pond. Cover structures can have varying levels of transparency for actinic light. It is noted that for most ponds, the benefits of a pond cover can typically be realized without needing to cover paddle wheel structures. The portion of the pond surface area corresponding to the paddle wheel is small relative to the total surface area and becomes proportionally smaller as the pond increases in size. Similarly, other structures in a pond that would be awkward to cover and that correspond to a small portion of the surface area can be left uncovered.

To facilitate algae growth and/or production of distillate boiling range products by the algae, a variety of nutrients are introduced into a pond. $CO_2$ is introduced to provide a source of carbon for the algae. Sources of phosphorous and nitrogen are also typically introduced. The amount of $CO_2$, phosphorous, nitrogen, and/or other nutrients or additives may be controlled in conjunction with available light intensity to induce a desired behavior by algae in the pond. Controlling the conditions allows for selection of conditions during some time periods that are favorable for increasing the total number of algae within a pond, while other selected conditions will favor production of storage compounds by the algae, such as starches, oils, or lipids.

After algae are grown and/or have produced a desired distillate boiling range product, the algae are harvested in preparation for extraction of the desired product. Typical growth conditions for algae correspond to relatively low weight ratios of algae to water in a pond. A harvesting step allows the algae and/or the desired product to be separated from a substantial portion of the water prior to further processing. The amount of water removed during harvesting or dewatering depends on the extraction process for recovering a distillate boiling range product from the algae.

Any convenient method can be used to dewater algae during harvesting. One or more centrifuges can be used to remove water. Other options for water removal, either alone, in combination with the one or more centrifuges, or in combination with each other include, but are not limited to, sedimentation, flocculation, coagulation, dissolved air flotation, and increasing the temperature of the algae-water sample.

After dewatering, the algae will typically still contain some water. This dewatered algae can be used as the input feed for a product extraction process. For a dewatered feed containing at least algae and water, the algae content of the feed can be at least about 5 wt %, or at least about 10 wt %, or at least about 20 wt %, or at least about 25 wt %, or at least about 30 wt %. The algae content of the feed can be about 50 wt % or less, or about 30 wt % or less, or about 25 wt % or less, or about 20 wt % or less. In terms of ratios, the ratio of water to algae in the feed can be at least about 1 to 1, or at least about 2 to 1, or at least about 3 to 1, or at least about 4 to 1. The ratio of water to algae can be about 25 to 1 or less, or about 20 to 1 or less, or about 10 to 1 or less. The algae content of the feed relative to the amount of water can be based on practical considerations regarding extraction of water from the source of the algae. Algae can be introduced into a reactor as a mixture or paste of algae and water. Alternatively, a dried form of algae can be introduced into a reactor along with sufficient water to reach a desired ratio of algae to water.

It is noted that the water present in an algae (or other biomass) feed can be either extracellular water or intracellular water. Intracellular water refers to water contained within the cell membrane of a cell, such as an algae cell. For an algae feed, a feed that is apparently relatively dry based on extracellular water can still contain a substantial portion of intracellular water. In the discussion below, references to the amount of water in a feed relative to the amount of algae are on the basis of dry algae that does not contain intracellular water. A freeze-dried algae is an example of an algae that does not contain intracellular water. For an algae that contains intracellular water, computing the ratio of water to algae requires determining the amount of intracellular water, as any intracellular water should count toward the weight of water and not the weight of algae. As a clarifying example, an algae sample could include no extracellular water and still have a water to algae ratio of about 1 to 1 or greater, or about 2 to 1 or greater, due to the amount of intracellular water in the algae. More generally, references below to the weight of algae refer to the weight of dry algae, excluding intracellular water.

Types of Algae

Algal sources for algae oils and for use in accordance with various aspects of the present invention can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. The algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmis, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

Algae oils, primarily lipids, are typically contained in algae in the form of membrane components, storage products, and metabolites. Certain algal strains, particularly microalgae such as diatoms and cyanobacteria, contain proportionally high levels of lipids. Algal sources for the algae oils can contain varying amounts, e.g., from 2 wt % to 60 wt % of lipids, based on total weight of the biomass itself.

Product Recovery

After harvesting algae, an oil recovery process can be used to separate one or more desired products from other material, such as residual biomass. The desired products can correspond to distillate boiling range molecules, molecules suitable for use as a fuel or fuel blending product after optional further processing, or other types of molecules. Various processes are available for separating one or more desired products from the remaining residue. One option is to use hydrothermal processing to rupture the algae cells and then separate out a desired product. Such hydrothermal processing can be enhanced by introducing one or more solvents, such as methanol, ethanol, or other alcohols, into the hydrothermal processing environment. Hydrothermal processing can also be enhanced by introducing an acid into the hydrothermal processing environment. Another option is to use an alcohol, such as ethanol, to extract desired products from the algae.

The total output from an oil recovery process will typically be a mixture of compounds. The mixture will include one or more oils or lipids that correspond to a desired product. The oils or lipids will be mixed with water and various residual solids from the algae. A multi-phase separation can be performed to separate the desired oils and lipids from the water and the residual solids. Optionally, after the oils or lipids are separated, the oils or lipids can undergo further processing. For example, an alcohol can be added to the oils or lipids to form a fatty acid alkyl ester.

Hydrothermal processing can be performed in a batch, semi-batch, or continuous processing environment. The reactor can be any type of batch reactor suitable for handling the processing conditions. Due to the potential presence of water at subcritical or supercritical conditions, stainless steel can be a suitable non-reactive material for the reactor walls. Other materials and/or coatings for the reactor surfaces can be used that are compatible with the reaction conditions described below. Examples of suitable reactors can include autoclaves, stirred tanks, or plough mixers. Alternatively, a bubble column could also be used. One possible advantage for batch or semi-batch type processing of an algae feed is that the algae feed, after removal of water, may have poor flow characteristics. For example, at an algae concentration relative to water of about 20 wt % (4 parts water to 1 part algae by weight), the resulting mixture can have the consistency of a paste. Such a paste could be difficult to move using pumps in a continuous flow type reactor.

Where the algae feed to hydrothermal processing is suitable for direct pumping, a continuous process can be used such as a plug-flow reactor configuration. The reactor size and flow rate are then matched to desired residence times and temperatures for the algae in the hydrothermal processing environment. Different mixing configurations include static mixers or Tee mixers. Due to the potential presence of water at subcritical or supercritical conditions, stainless steel is a suitable choice as a non-reactive material for the reactor walls. Other materials and/or coatings for the reactor surfaces that are compatible with the reaction environment can also be used. Options for continuous processing reactors include fixed bed, open pipe, or ebullating bed reactors.

As an example, a batch reactor can be used for hydrothermal processing of an algae feed. A portion of algae feed mixed with water can be introduced into the reactor. The reactor can then be purged (if necessary) to remove any oxygen containing gases. Optionally, a partial pressure of an inert gas and/or a reducing gas can then be introduced into the reactor. Examples of suitable reducing gases can include hydrogen, while suitable inert gases can include nitrogen. The partial pressure of additional gas introduced into the reactor can be at least about 25 bar (2.5 MPa), or at least about 40 bar (4.0 MPa), or at least about 50 bar (5.0 MPa). The partial pressure of gas introduced into the reactor can be 100 bar (10.0 MPa) or less, or 75 bar (7.5 MPa) or less, or 50 bar (5.0 MPa) or less. Note that introducing a reducing gas can correspond to saturating the water for the hydrothermal treatment with the reducing gas.

Another potential addition for the hydrothermal processing environment is one or more oxygenates such as an alcohol or an acid. Acids and alcohols in the hydrothermal processing environment improve the yield of hydrocarbon product as well as reducing the nitrogen content of the hydrocarbon product. This latter advantage may be lost, however, if the harvested algae is exposed to the hydrothermal processing conditions at temperatures greater than about 250° C. or for processing times greater than about 60 minutes. Suitable alcohols include any convenient alcohol, such as methanol or ethanol. The amount of alcohol introduced into the reaction environment can be approximately equal to the amount of dry algae on a weight basis. More generally, the weight ratio of alcohol to algae to provide a solvent benefit during hydrothermal processing can range from about 1:10 to about 10:1. Suitable acids include acids that are compatible with being recycled to an algae growth environment, such as phosphoric acid or acetic acid. The concentration of acid to provide a benefit during hydrothermal processing can range from about 0.4 M to about 5.0 M.

After introducing the algae, water, any oxygenate additive, and any additional reducing and/or inert gases, the batch reactor can be sealed. The conditions for hydrothermal processing can be selected to recover oil while generating a residual product containing at least a portion of (potentially) fermentable material. The temperature of the reactor can be raised to at least about 50° C., or at least about 80° C., or at least about 150° C., or at least about 250° C., or at least about 275° C., or at least about 300° C. The temperature of the reactor can be raised to about 500° C. or less, or about 400° C. or less, or about 380° C. or less, or about 350° C. or less, or about 300° C. or less, or about 275° C. or less. The pressure in the reactor can be at least about 1 bar (0.1 MPa), or at least about 25 bar (2.5 MPa), or at least about 50 bar (5.0 MPa), or at least about 100 bar (10.0 MPa). The pressure can be about 300 bar (30.0 MPa) or less, or about 250 bar (25.0 MPa) or less, or about 225 bar (2.25 MPa) or less, or about 200 bar (20.0 MPa) or less. A desirable combination of temperature and pressure will depend on the desired balance between oil recovery and preserving additional utility for the residual solids, as well as the type of algae.

In some cases, the hydrothermal processing is performed under higher severity conditions. The higher severity conditions result in greater oil recovery, but generate reduced amounts of fermentable material in residual solids while also generating ammonia. Suitable higher severity conditions include temperatures above about 300° C. and pressures of at least about 1500 psig (10.3 MPag).

Another option during processing can be the use of a hydrothermal processing catalyst. A hydrothermal processing catalyst can be a catalyst that is soluble in the hydrothermal reaction environment, or the catalyst can be in the form of catalyst particles in the reaction environment. The catalyst particles can optionally be a supported catalyst, with a catalytic material supported on a substrate.

One option for a supported catalyst can be a supported noble metal catalyst. The noble metal can be Pt, Pd, Rh, Ru, Ir, or a combination thereof. The support for the catalyst can be a hydrothermally stable support. Examples of suitable supports can include refractory oxides such as titania or zirconia. Silica or activated carbon can also form a suitable support material. Still other options for a support can include magnesium oxides, hydrotalcites, or other various types of clays. Yet another option can be a support composed of a mixture of one or more of the above supports, such as a mixture of two or more of titania, zirconia, and silica. Alternatively, the support material can be substantially free of alumina, meaning that the support material contains no alumina, or contains less than 0.01 wt % of alumina, or less than 0.1 wt % of alumina, or less than 1 wt % of alumina.

Another supported catalyst option can be to use a basic metal or mixed metal oxide with or without a noble metal. Examples of catalysts without a noble metal can include magnesium oxide, hydrotalcites, and potassium supported on titania or zirconia.

Relative to the amount of algae, the amount of supported catalyst in the reactor can be at least about 0.05 wt %, or at least about 0.1 wt %, or at least about 1 wt %, or at least about 2.5 wt %, or at least about 5 wt %. The amount of supported catalyst in the reactor can be about 20 wt % or less relative to the amount of algae, or about 15 wt % or less, or about 10 wt % or less.

The amount of metal supported on the catalyst can vary as well. Relative to the weight of the catalyst, the amount of a noble metal supported on the catalyst can be at least about 0.1 wt. % per weight of catalyst, or at least about 0.5 wt. %, or at least about 0.6 wt. %, or at least about 0.75 wt %, or at least about 1.0 wt %. The amount of noble metal supported on a catalyst can be about 1.5 wt % or less, or about 1.0 wt % or less, or about 0.75 wt % or less, or about 0.6 wt % or less. More generally, the amount of metals, either individually or in mixtures, on a catalyst support can be at least about 0.1 wt %, or at least about 0.25 wt %, or at least about 0.5 wt %, or at least about 0.6 wt %, or at least about 0.75 wt %, or at least about 1 wt %, or at least about 2.5 wt %, or at least about 5 wt %. The amount of metals, either individually or in mixtures, on a catalyst support can be about 35 wt % or less, or about 20 wt % or less, or about 15 wt % or less, or about 10 wt % or less, or about 5 wt % or less.

As an alternative oil recovery process, an alcohol such as methanol, ethanol, or butanol can be directly used for solvent extraction of hydrocarbons from algae. Optionally, the solvent extraction may be performed under supercritical conditions. The solvent extraction can occur in a batch stirred tank reactor, in a slurry bubble column, or as a countercurrent wash within a continuous flow centrifuge. The solvent extraction allows for separation of desired distillate boiling range products from algae husks or other residual solids. The solvent can then be recovered from the desired product via boiling point separation such as in a flash drum or distillation column. The amount of solvent can be roughly equal to the weight of the dry algae. More generally, the amount of solvent can be from about 1.0 to 10.0 times the weight of the dry algae, such as at least about 2.0 times the weight of the dry algae. Suitable temperatures include temperatures from about 15° C. (or another ambient temperature) to about 80° C., such as at least about 40° C. The extraction time can be selected to balance the time required for extraction with the extraction efficiency. Increased amounts of solvent and/or increased extraction temperatures will typically reduce the reaction time required to achieve a desired level of extraction. Suitable extraction times range from about 0.25 hours to about 24 hours, such as from about 2 hours to about 16 hours, and preferably from about 6 hours to about 12 hours.

Other options as solvents for solvent extraction include alcohols, hydrocarbon solvents, aromatic solvents, acetone, glycerol, alcohol, hexane, heptane, methylpentane, toluene, or methylisobutylketone. If the solvent is an alcohol, examples of alcohols include, but are not limited to, methanol, propanol, ethanol, and isopropanol. Alternatively, a solvent can be selected as a solvent for hydrophobic extraction. In hydrophobic extraction, a solvent is selected so that the extraction solvent is either immiscible in water, or a partition is formed so that only a portion of the solvent is in the water phase. Examples of suitable solvents suitable include nonpolar organic liquids, such as aliphatic hydrocarbons, or various petroleum ethers. Other suitable solvents include esters, ethers, ketones, nitrated and chlorinated hydrocarbons. Examples of solvents include carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, or 2,2,4-trimethylpentane.

Hydrolysis or Other Pre-Fermentation Treatment of Residual Solids

Extraction and separation of one or more desired products will typically result in generation of residual biomass, typically in the form of residual solids. The residual solids correspond to algal husks and other solids from the algae used to generate the desired hydrocarbons. Potentially, some residual biomass may also be dissolved in the aqueous phase after hydrolysis. Because the residual biomass corresponds to the remnants of the original algae, the residual biomass represents a suitable source of nutrients for future algae growth. Additionally or alternately, under some types of oil recovery, the residual biomass will also contain fermentable solids (or the precursors of fermentable solids) that can be used for generation of oxygenates. The oxygenates can be used in other parts of the algae processing system.

The residual solids (or other residual biomass, such as residual biomass dissolved in the aqueous phase) will typically include some fermentable material, or more commonly, potentially fermentable material. As noted above, the amount of fermentable material will vary depending on a variety of factors. Often, it will be desirable and/or economically valuable to use the fermentable material to form oxygenate products. Prior to fermentation, the potentially fermentable material is pretreated, such as by hydrolysis, to allow for subsequent fermentation. Polysaccharides represent a type of potentially fermentable material. A hydrolysis process allows the polysaccharides and other potentially fermentable material to be broken down into starches, saccharides, or other sugars. The starches, saccharides, or other sugars are then fermented using a suitable yeast. Any convenient type of hydrolysis conditions may be used to convert residual solids into fermentable material. An oxygenate such as methanol or ethanol or an organic acid may also be added to the hydrolysis reaction to facilitate conversion of potentially fermentable material into fermentable material. A typical set of hydrolysis conditions involves exposing potentially fermentable material to a heated aqueous environment in the presence of one or more enzymes, one or more acids, or a combination of acid(s) and enzyme(s). Temperatures from 35° C. to 90° C. may be suitable, depending on the type of enzyme used. The addition of acids, such as organic acids created from fermentation, can facilitate the hydrolysis process. Other examples of hydrolysis processes include steam explosion processes and base catalyzed processes (such as those involving ammonia/ammonium hydroxide). Complete hydrolysis of potentially fermentable material may require multiple hydrolysis processes performed in sequence. For example, an acid hydrolysis process can be followed by an enzyme hydrolysis process.

After hydrolysis, another separation may be performed to separate water soluble, fermentable material from insoluble by-products.

Fermentation and Oxygenate Generation

After hydrolysis, fermentable material is then fermented using a suitable yeast (e.g., Saccharomyces cerevisiae) or other bacteria to form oxygenates. The type of oxygenate formed is typically dependent on the type of yeast or bacteria. Possible oxygenates include alcohols, such as methanol, butanol, or ethanol, or organic acids such as acetic acid. Examples of yeast or bacteria include Enterobaceriae, which can produce organic acids, and the yeast Saccharomyces Cerevisiae which is useful for ethanol production.

During fermentation, the yeast or bacteria consume the fermentable material and form oxygenates, $CO_2$, and heat. Fermentation also typically results in formation of some residual by-products. A separator can be used to separate out the gas phase $CO_2$, the aqueous phase oxygenates, and the now insoluble by-products. The $CO_2$ can be recycled for any convenient use. For example, the $CO_2$ can be returned to an algae growth pond for use in growth of a new batch of algae. If any additional $CO_2$ is provided from other biomass sources, this allows for growth of truly renewable algae that do not depend on fossil fuel sources of carbon.

The aqueous phase containing oxygenates is then distilled to concentrate the desired oxygenates in the aqueous environment. The water removed during distillation can be recycled, for example, to an algae growth pond. The oxygenates can be used in a variety of ways. If desired, the fermentation conditions may be selected to form alcohols, acids, or a combination thereof. The alcohols and/or acids are then recycled to an oil recovery process that uses hydrothermal processing and/or used to pre-treat fermentable materials. The alcohols and/or acids allow for improved recovery of the desired oils or lipids, as well as potentially reducing the nitrogen content of the recovered hydrocarbons. Another option is to focus the fermentation on alcohol production and use the alcohol for alcohol extraction of the oils or lipids from the algae. Still another option is to use the generated oxygenates as a product, thus increasing the overall yield of products from the algae processing system.

Processing of Product Solids for Recycle of Nutrients

In addition to fermentation of the residual solids to form oxygenates, a variety of algae growth nutrients can be recovered from the residual solids. Nutrient recovery can be performed on the by-products from hydrolysis of the residual solids and/or on the by-products from fermentation.

Several options are available for nutrient recycle from the residual solids. Often, the by-products from hydrolysis and/or fermentation are in a relatively accessible form. An accessible form may correspond to nitrogen that is present as basic nitrogen and phosphorus present in the form of phosphates. In such cases, the by-products can be exposed to an acid wash involving an acid such as acetic acid, phosphoric acid, or sulfuric acid. Preferably, a weak acid such as acetic acid is used for the acid wash. The acid wash is used to neutralize the pH of the by-products prior to recycling the by-products as nutrients for the algae growth pond(s).

Alternatively, a digester can be used to increase the nutrient yield. In a digestion process, the by-products are exposed to bacteria, such as methanotropic bacteria, that converts the remaining by-products into a more usable form. Digestion by bacteria will typically generate gas phase products including $H_2$, small organics such as $CH_4$, and $CO_2$. The $H_2$ and small organic gas phase products can be used as a fuel source. The remaining digestion products, including the gas phase $CO_2$ are typically more suitable for recycle to an algae growth pond. Still another option is to use residual biomass and/or other biomass as a feed for a gasifier, as described in other portions of this description.

Additional Processing of Product Molecules

The type of desired product molecules recovered from an algae source or non-algal source will be dependent on the nature of the biomass source. In particular, different types of algae can generate a wide variety of distillate boiling range molecules, molecules suitable for use as a fuel or fuel blending product after optional further processing, or other types of product molecules. Possible products include fatty acids, aldehydes, ketones, and other molecules including one or more functional groups containing oxygen and/or nitrogen heteroatoms. The products may optionally further include one or more degrees of unsaturation.

While it is possible that the product molecules recovered from algae will be directly suitable for use as a fuel, fuel additive, lubricant, lubricant additive, or other chemical product, more typically the product molecules will undergo further processing prior to use. One type of additional processing can be further separation and/or purification of the product molecules. Other types of further processing can involve performing reactions to change the boiling range or modify the functional groups in the molecules. For example, many types of algae produce distillate boiling range products that have boiling points above a typical diesel maximum boiling point of about 650° F. (343° C.) to about 750° F. (399° C.). Such molecules can be chemically reacted to generate lower boiling species. Another option can be to convert product molecules to a format that is compatible with conventional processing systems. Many algae produce fatty acids as potential product molecules. The fatty acids can be reacted with alcohols to form fatty acid alkyl esters, for use in a refinery with existing process flows for handling fatty acid alkyl esters. Still another option can be to crack or otherwise reduce the boiling point of the products to temperatures below the distillate boiling range. This could allow for formation of naphtha boiling range compounds and/or formation of small molecules for use as a feed for polymer formation. Methods and systems of the present invention including such further processing steps are within the scope of the various aspects of the present invention.

Any of the methods described above can be performed by a biofuels production system. Further, any of the methods described above can be performed alone or in combination. Accordingly, another aspect of the invention is a biofuels production system that performs one or both of the methods described above.

Additional Embodiments

Additionally or alternately, the present invention can include one or more of the following embodiments.

Embodiment 1. A method for generating a fuel or fuel blending product, comprising: providing a feed comprising algae-derived biomass from an algae growth environment; recovering a fuel or fuel blending product and a residual product from the algae-derived biomass; performing a gasification process on at least a portion of the residual product, the gasification process resulting in at least a gas phase output stream and a gasification residue stream, the gas phase output stream comprising $H_2$ and CO; purifying the gas phase output stream by removing at least a portion of one or more contaminant compounds different from $H_2$ and CO; and converting at least a portion of the purified gas phase output stream into one or more organic molecules.

Embodiment 2. A method according to Embodiment 1, wherein converting at least a portion of the purified gas phase output stream into one or more organic molecules comprises synthesizing methanol using at least a portion of the purified gas phase output stream.

Embodiment 3. A method according to Embodiment 2, wherein recovering a fuel or fuel blending product is performed in the presence of at least a portion of the synthesized methanol.

Embodiment 4. A method according to Embodiments 2 or 3, further comprising synthesizing fatty acid methyl esters from at least a portion of the synthesized methanol and a feed containing triacylglycerols, the feed containing triacylglycerols optionally comprising at least a portion of the recovered fuel or fuel blending product.

Embodiment 5. A method according to any of the above embodiments, wherein converting at least a portion of the purified gas phase output stream into one or more organic molecules comprises performing a Fischer-Tropsch synthesis process using at least a portion of the purified gas phase output stream, the Fischer-Tropsch synthesis process generating one or more alkane products and one or more oxygenate by-products.

Embodiment 6. A method according to Embodiment 5, wherein recovering a fuel or fuel blending product is performed in the presence of at least a portion of the one or more oxygenate by-products.

Embodiment 7. A method according to any of the above embodiments, wherein at least a portion of the gas phase output stream is used as a fuel gas.

Embodiment 8. A method according to any of the above embodiments, further comprising recycling at least a portion of the one or more contaminant compounds, at least a portion of the gasification residue, or a combination thereof to the algae growth environment, the gasification residue optionally being washed with an acid prior to recycling.

Embodiment 9. A method according to Embodiment 8, wherein the recycled portion of the one or more contaminant compounds comprises $NH_3$, $CO_2$, or a combination thereof.

Embodiment 10. A method according to any of the above embodiments, further comprising modifying the composition of the gas phase output stream from the gasification process using a water gas shift reaction.

Embodiment 11. A method according to any of the above embodiments, wherein the fuel or fuel blending product and the residual product are recovered from the algae-derived biomass and at least one additional biomass feed.

Embodiment 12. A method according to any of the above embodiments, wherein the gasification process is further performed on at least one additional biomass feed.

Embodiment 13. A method according to any of the above embodiments, wherein conversion of at least a portion of the purified gas phase output stream into one or more organic molecules results in production of oxygenates, at least a portion of the oxygenates being used as a reagent in the recovering of a fuel or fuel blending product.

Embodiment 14. A method for generating biofuels, comprising: growing algae in an algae growth environment; recovering a first fuel or fuel blending product and a residual product from an algae-derived biomass feed from the algae growth environment; recovering a second fuel or fuel blending product and a second residual product from a second biomass feed; performing a gasification process on at least a portion of the second residual product, the gasification process producing at least a first gas phase output stream and a gasification residue, the first gas phase output stream comprising $NH_3$, $CO_2$, or a combination thereof; and recycling at least a portion of the first gas phase output stream or the gasification residue stream to the algae growth environment.

Embodiment 15. A method according to Embodiment 14, wherein the second fuel or fuel blending product is a fatty acid alkyl ester.

Embodiment 16. A method according to Embodiment 14 or 15, further comprising processing the first fuel or fuel blending product to form fatty acid alkyl esters.

Embodiment 17. A method according to any of Embodiments 14 to 16, wherein the gasification process further produces a second gas phase output stream comprising $H_2$ and CO, the method further comprising converting at least a portion of the purified gas phase output stream into one or more organic molecules, the conversion resulting in the production of at least one oxygenate that is used as a reagent in recovery of the first fuel or fuel blending product or as a reagent in recovery of the second fuel or fuel blending product.

We claim:

1. A method for generating a fuel or fuel blending product, comprising:
   providing a feed comprising algae-derived biomass from an algae growth environment;
   recovering a fuel or fuel blending product and a residual product from the algae-derived biomass;
   performing a gasification process on at least a portion of the residual product, the gasification process resulting in at least a gas phase output stream and a gasification residue stream, the gas phase output stream comprising $H_2$ and CO;
   purifying the gas phase output stream by removing at least a portion of one or more contaminant compounds different from $H_2$ and CO; and
   converting at least a portion of the purified gas phase output stream into one or more organic molecules,
   wherein conversion of at least a portion of the purified gas phase output stream into one or more organic molecules results in production of oxygenates, at least a portion of the oxygenates being used as a reagent in the recovering of a fuel or fuel blending product.

2. A method for generating a fuel or fuel blending product, comprising:
   providing a feed comprising algae-derived biomass from an algae growth environment;
   recovering a fuel or fuel blending product and a residual product from the algae-derived biomass;
   performing a gasification process on at least a portion of the residual product, the gasification process resulting in at least a gas phase output stream and a gasification residue stream, the gas phase output stream comprising $H_2$ and CO;
   purifying the gas phase output stream by removing at least a portion of one or more contaminant compounds different from $H_2$ and CO; and
   converting at least a portion of the purified gas phase output stream into one or more organic molecules,
   wherein converting at least a portion of the purified gas phase output stream into one or more organic molecules comprises synthesizing methanol using at least a portion of the purified gas phase output stream.

3. The method of claim 2, wherein recovering a fuel or fuel blending product is performed in the presence of at least a portion of the synthesized methanol.

4. The method of claim 2, further comprising synthesizing fatty acid methyl esters from at least a portion of the synthesized methanol and a feed containing triacylglycerols.

5. The method of claim 4, wherein the feed containing triacylglycerols comprises at least a portion of the recovered fuel or fuel blending product.

6. The method of claim 1, wherein converting at least a portion of the purified gas phase output stream into one or more organic molecules comprises performing a Fischer-Tropsch synthesis process using at least a portion of the purified gas phase output stream, the Fischer-Tropsch synthesis process generating one or more alkane products and one or more oxygenate by-products.

7. The method of claim 6, wherein recovering a fuel or fuel blending product is performed in the presence of at least a portion of the one or more oxygenate by-products.

8. The method of claim 6, further comprising using at least a portion of the purified gas phase output stream to synthesize methanol.

9. The method of claim 1, wherein at least a portion of the gas phase output stream is used as a fuel gas.

10. The method of claim 1, further comprising recycling at least a portion of the one or more contaminant compounds, at least a portion of the gasification residue stream, or a combination thereof to the algae growth environment.

11. The method of claim 10, wherein the recycled portion of the one or more contaminant compounds comprises $NH_3$, $CO_2$, or a combination thereof.

12. The method of claim 10, wherein recycling at least a portion of the gasification residue stream comprises washing the at least a portion of the gasification residue stream with an acid prior to recycling.

13. The method of claim 1, further comprising modifying the composition of the gas phase output stream from the gasification process using a water gas shift reaction.

14. The method of claim 1, wherein the fuel or fuel blending product and the residual product are recovered from the algae-derived biomass and at least one additional biomass feed.

15. The method of claim 1, wherein the gasification process is further performed on at least one additional biomass feed.

16. A method for generating biofuels, comprising:
   growing algae in an algae growth environment;

recovering a first fuel or fuel blending product and a residual product from an algae-derived biomass feed from the algae growth environment;

recovering a second fuel or fuel blending product and a second residual product from a second biomass feed, the second biomass feed comprising at least one of plant biomass, cellulosic biomass, lignocellulosic biomass, animal biomass, or waste product biomass;

performing a gasification process on at least a portion of the second residual product, the gasification process producing at least a first gas phase output stream and a gasification residue, the first gas phase output stream comprising $NH_3$, $CO_2$, or a combination thereof; and recycling at least a portion of the first gas phase output stream or the gasification residue stream to the algae growth environment.

17. The method of claim 16, wherein the second fuel or fuel blending product is a fatty acid alkyl ester.

18. The method of claim 16, further comprising processing the first fuel or fuel blending product to form fatty acid alkyl esters.

19. The method of claim 16, wherein the gasification process further produces a second gas phase output stream comprising $H_2$ and CO, the method further comprising converting at least a portion of the purified gas phase output stream into one or more organic molecules, the conversion resulting in the production of at least one oxygenate that is used as a reagent in recovery of the first fuel or fuel blending product or as a reagent in recovery of the second fuel or fuel blending product.

* * * * *